US008652829B2

(12) United States Patent
Bellalou et al.

(10) Patent No.: US 8,652,829 B2
(45) Date of Patent: Feb. 18, 2014

(54) ROBOTIZED PLATFORM FOR CELL CULTURES IN MINIATURE REACTOR BATTERIES, EQUIPPED WITH A SYSTEM FOR REAL TIME MEASUREMENT OF CELLULAR TURBIDITY OR OTHER OPTICAL PROPERTIES

(75) Inventors: Jacques Bellalou, Paris (FR); Emmanuel Frachon, Charenton le Pont (FR); Alain Meier, Charenton le Pont (FR); Robert A. Longin, Paris (FR)

(73) Assignee: Institut Pasteur, Paris (FR)

( * ) Notice: Subject to any disclaimer, the term of this patent is extended or adjusted under 35 U.S.C. 154(b) by 1235 days.

(21) Appl. No.: 10/517,776

(22) PCT Filed: Jun. 27, 2003

(86) PCT No.: PCT/FR03/02006
§ 371 (c)(1),
(2), (4) Date: Jul. 19, 2005

(87) PCT Pub. No.: WO2004/003569
PCT Pub. Date: Jan. 8, 2004

(65) Prior Publication Data
US 2006/0001865 A1 Jan. 5, 2006

(30) Foreign Application Priority Data
Jun. 28, 2002 (CA) ..................................... 2391641

(51) Int. Cl.
*C12M 1/36* (2006.01)
(52) U.S. Cl.
CPC ..................................... *C12M 41/48* (2013.01)
USPC ....................................... 435/286.2; 356/246

(58) Field of Classification Search
USPC ....................... 435/286.2; 356/246, 250, 254; 250/208.6, 461.2, 553, 559.12, 559.16, 250/578.1
See application file for complete search history.

(56) References Cited

U.S. PATENT DOCUMENTS

| 3,837,746 | A | * | 9/1974 | Acker et al. .................. 356/440 |
| 5,314,825 | A | | 5/1994 | Olson et al. |
| 6,307,630 | B1 | | 10/2001 | Banerjee |
| 6,723,554 | B1 | * | 4/2004 | Gaillon et al. ............. 435/288.7 |
| 2002/0155619 | A1 | * | 10/2002 | Kurihara et al. .............. 436/172 |
| 2004/0033166 | A1 | * | 2/2004 | Arnowitz et al. .......... 422/82.05 |

FOREIGN PATENT DOCUMENTS

| WO | 93/20612 | 10/1993 |
| WO | 99/04228 | 1/1999 |
| WO | 99/27349 | 6/1999 |

* cited by examiner

*Primary Examiner* — Michael Hobbs
(74) *Attorney, Agent, or Firm* — Law Office of Salvatore Arrigo and Scott Lee, LLP

(57) ABSTRACT

An automated and robotized platform includes a battery of miniature reactors to contain cell cultures. The platform includes an external sensor to measure an optical property of each cell culture contained in each miniature reactor. The platform also includes a mobile sensor-holder to receive the external sensor. The sensor-holder includes a sensor driving element to move the external sensor from one miniature reactor to another and to measure in real time the at least one optical property. The platform further includes a controlling and processing element to receive real time measurements of the optical property from the external sensor and to provide real time control of a movement of the mobile sensor-holder.

15 Claims, 17 Drawing Sheets

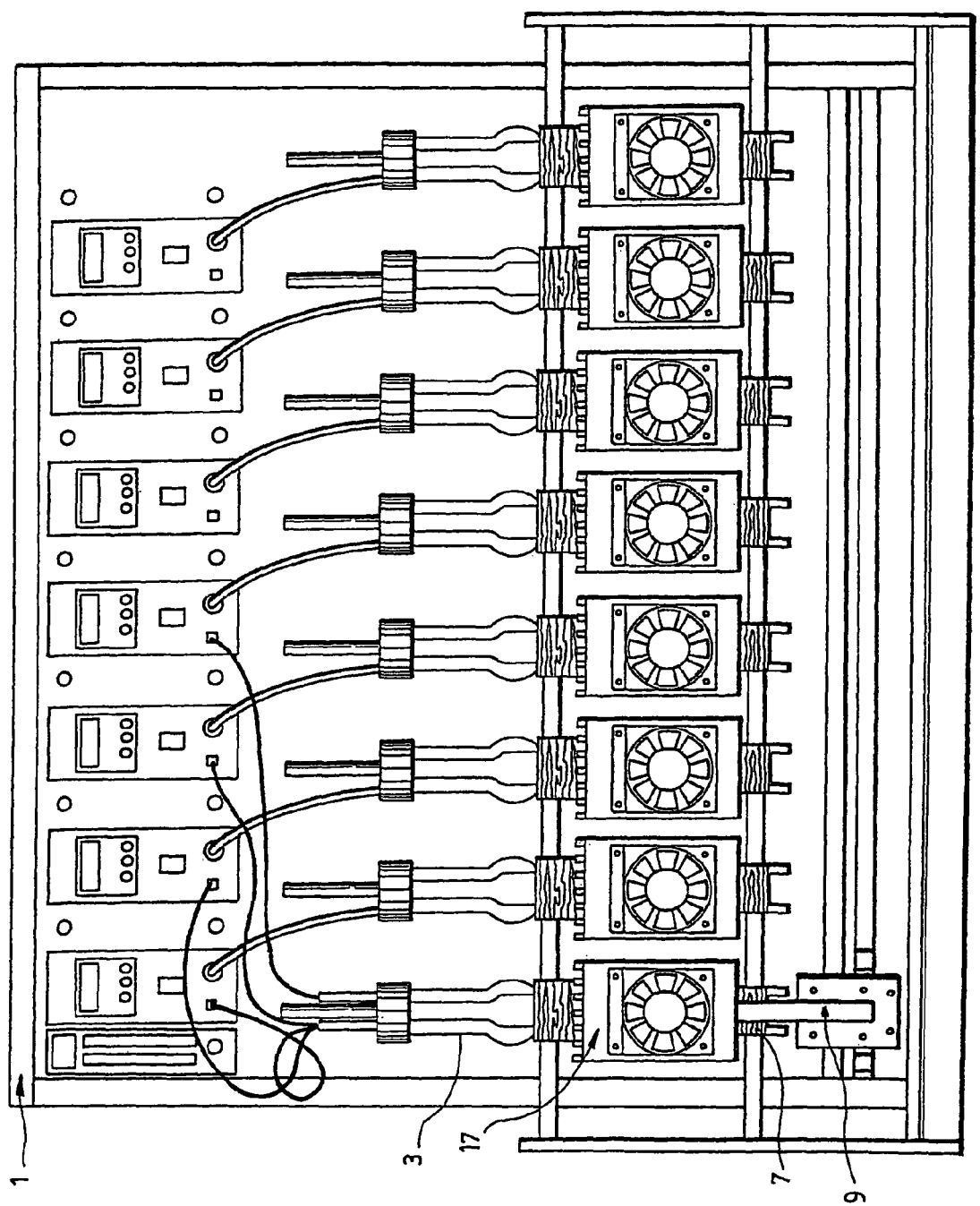

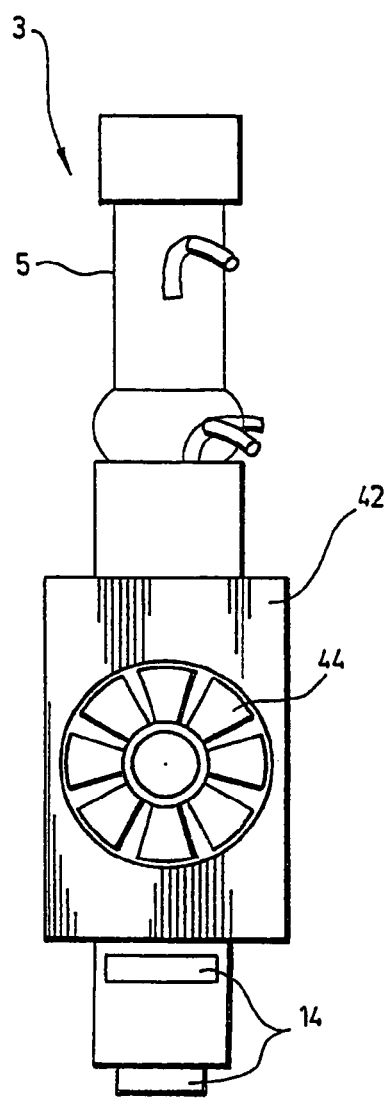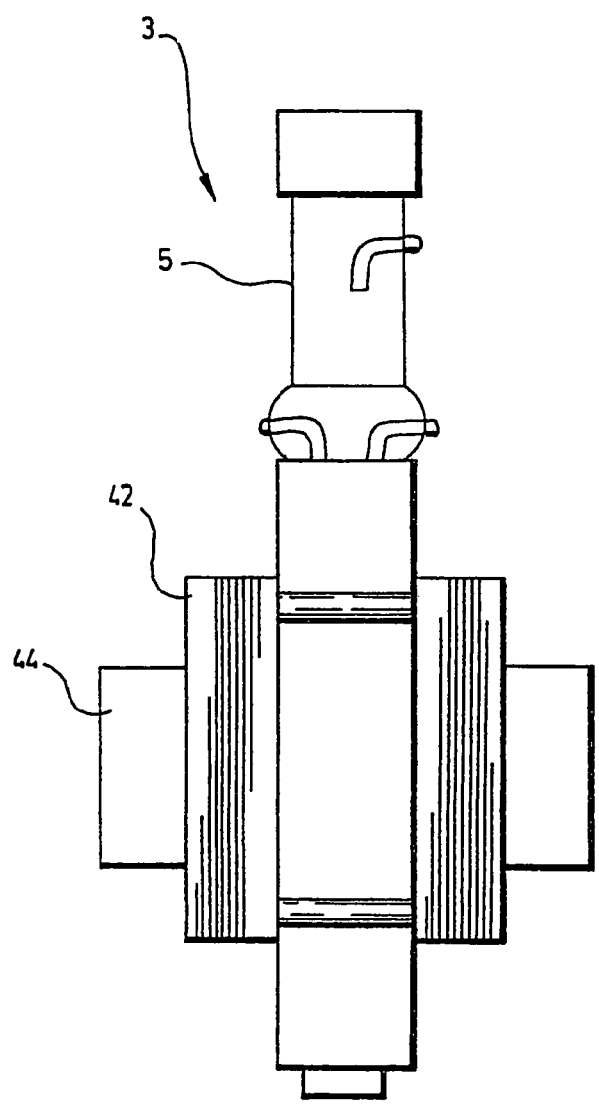
FIG. 9A
FIG. 9B

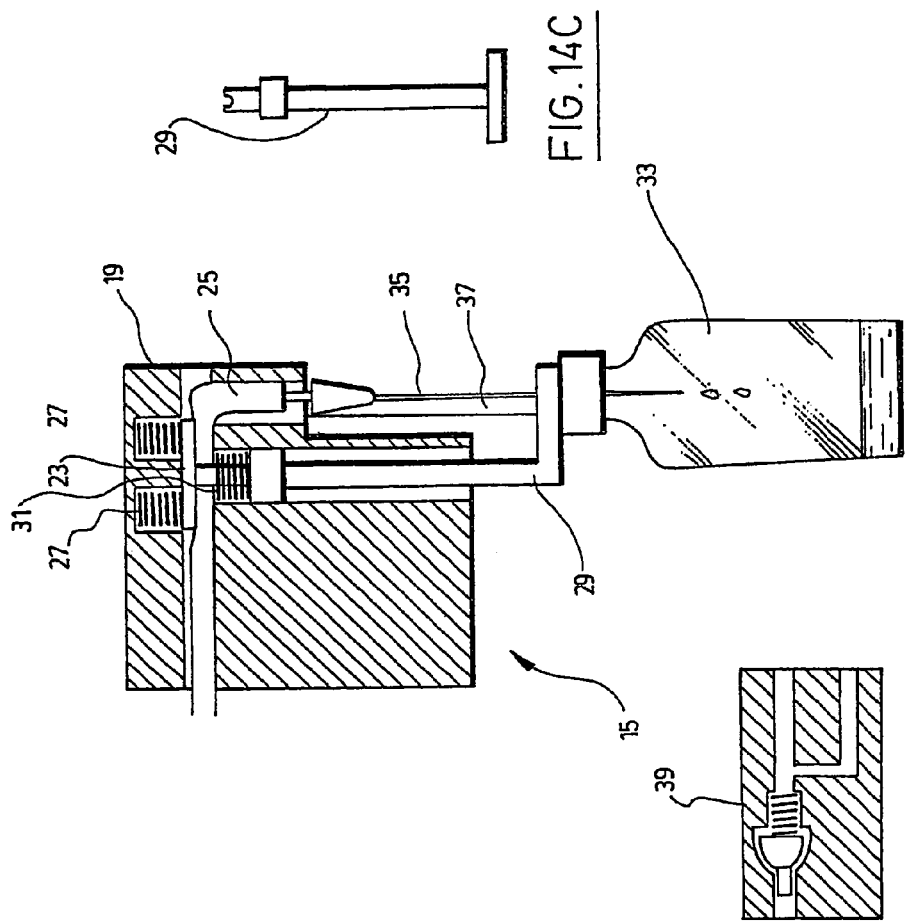
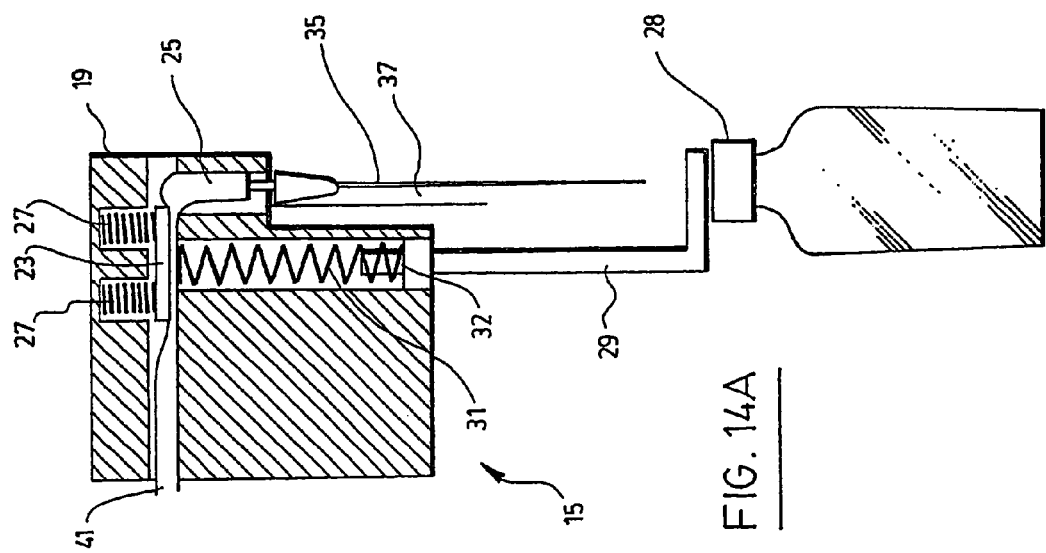

ROBOTIZED PLATFORM FOR CELL CULTURES IN MINIATURE REACTOR BATTERIES, EQUIPPED WITH A SYSTEM FOR REAL TIME MEASUREMENT OF CELLULAR TURBIDITY OR OTHER OPTICAL PROPERTIES

CONTEXT OF THE INVENTION a) Field of the Invention

The invention relates to an automated system for monitoring and regulating cell cultures contained within a miniature reactor battery allowing, inter alia, for injection and sampling in cultures.

The invention also relates to a system and a process for real time measuring optical properties of cell cultures contained within a miniature reactor battery. Such optical properties could include, amongst others, turbidity.

b) Prior Art Short Description

In numerous biology laboratories and also in the biotechnology industries, it is often required to cultivate micro-organisms in a liquid medium and to measure cell concentration at various culture steps. The most practical and widely used methods for evaluating the culture cell concentrations lie on the optical properties of the latter.

Known Cell Culture Systems

In the field of microbial culture technologies, it is observed that there are mainly three types of cultures: the cultures at the scale of research laboratories or in research and development; the cultures in conventional fermentors having as for objectives to optimize and produce; and the battery culture technologies.

The cultures at the scale of laboratories are achieved in micro-plates, in tubes or in stirred vials and make use of low volumes and of simple use equipment. They make it possible to conduct a large number of trials in parallel. However, the growth conditions are not optimum because of the nutritional limits imposed to cultures by the equipment to be used. There is little possibility to monitor and regulate the culture parameters, and this, consequently, leads to numerous standardization and reproducibility problems. Such techniques often suffer from some empiricism.

The cultures in conventional fermentors allow, in an environment being perfectly monitored by the use of sensors, for cultures to be made in non limiting conditions. However, the equipment is sophisticated, expensive and with a quite complicated implementation; the medium minimal volume remains high (0.5 liters) and does not easily allow for a large number of trials to be made in parallel. The automation is restricted and only applies to the reactor being cultured. Such an equipment type most often requires a research worker being trained in such technologies. The optical reading systems are expensive and bulky.

The battery culture technologies, as marketed by companies such as DASGIP [Unitron-pro$^{MC}$ Models (16×500 ml) or Stimmer-pro$^{MC}$ (8, 12, 16×150 to 300 ml)] or INFORS ([Profors$^{MC}$ Model (up to 16×150 ml)], offer an equipment monitoring as many as 16 cultures in aerated vials or mini-reactors, with measurement and regulation of the pH, the pO$_2$ and the temperature. The purpose of such equipment is mainly to be able to achieve easily, in standardized conditions, parallel cultures and to give a reply to the nutritional limitations encountered for cultures in badly aerated vials. However, such devices do not measure turbidity in line and consequently are not adapted for a fully automated operation based on the direct measurement of such a key parameter.

The most often implemented experimental steps in the field of industrial or biomedical bacteriology share in common the following objectives of:

cultivating numerous micro-organism strains with a view to comparing the performance thereof, followed by the selection of the strain being the most adapted for the method under consideration;

producing, at high levels, molecules such as recombinant proteins; and transferring the optimization results of the most important culture parameters of a given method, from a laboratory scale to a pilot production scale.

Such various steps are generally subjected to the same technical difficulties, as no one of the existing technologies, offering each respective interests, can fully meet the currently existing requirements and constraints. Such requirements originate from the very large discrepancy of the strains to be cultivated (different nutritional requirements, temperature, etc) and from the sequences of heterologous genes to be expressed in such strains.

There is therefore a need for a miniature and automated system for cell cultures adapted to meet all those requirements.

The present invention meets the above described needs and other needs as will be obvious to the man of the art from reading the present disclosure of the invention.

Known Systems Aiming at Measuring the Turbidity

Amongst the existing turbidimeters, are to be distinguished discontinuous or manual measurement devices, which are used for repeatedly measuring the light being emitted and/or reflected by a liquid medium, and the in line measurement devices, wherein turbidity-measuring probes are introduced within the liquid medium and are connected with a recording system.

The discontinuous measurement devices, such as nephelometers, calorimeters, spectrophotometers and mixed turbidimeters, do not allow, as far as most of them are concerned, for high turbidities to be measured. Such mixed turbidimeters were designed for covering a larger turbidity range, but these are expensive devices.

The in line turbidimeters, the measurement ranges of which can be quite large, have the inconvenient to require large culture volumes (from 250 ml up) because of the bulk of the probes being introduced within the cultures, limiting thus their use within miniature fermentors. In addition, the fermentor cultures are generally aerated and stirred, leading thus to the formation of numerous bubbles strongly disturbing the turbidity measurements. Such devices also suffer from their high cost.

Other existing direct measurement turbidimeters are expensive and difficult to use because their sensors need to be autoclaved, suffer from fouling and offer a less extended reading range. Such turbidimeters require, for each culture, different sensors inserted in the reactor and those are subjected to drifts during their operation.

Other existing current systems lie on indirect assessments of the bacterial density through measuring various culture parameters (pH, oxygen consumption, redox potential, substrate concentrations, etc.).

The International Patent Application WO 99/27349 (GAILLON et al.) discloses a sensor for the continuous measurement of culture turbidity. However, such a device is static and each reactor must be provided with its own sensor consisting in a particular pair of diodes (emitting/receiving diodes). Because of the mutual diode sensitivity and performance difference, it has been found difficult to accurately calibrate such sensors. Indeed, it is difficult to obtain, through the various sensors, the same response for a given turbidity suspension.

Nowadays, there exists no automated and mobile system, being not bulky, inexpensive and able to measure accurately the turbidity of microbial cultures made in tubes or in stirred reactors, on a large value range.

There is consequently a need for a system for measuring the optical properties of cell cultures, being free of the disadvantages of the known prior art devices, being not very bulky, with a reasonable price, and able to accurately measure, in real time, the turbidity of microbial cultures achieved in parallel on a large value range.

SUMMARY OF THE INVENTION

An object of the present invention is to provide a platform for cell cultures and a method for measuring the optical properties of cell cultures, being free of the disadvantages of the known prior art devices.

In particular, an object according to a preferred aspect of the present invention is to provide a little bulky system, with a reasonable cost, and able to accurately measure in real time the turbidity of various cell cultures simultaneously achieved on a wide value range.

One of the objects of the present invention is to provide a miniature and automated platform for cell cultures conducted in parallel and having the same performance as the laboratory fermentors.

The present invention thus relates to an automated and robotized platform comprising a battery of miniature reactors, each containing a cell culture, the platform comprising:
  an external sensor for measuring at least an optical property of each cell culture contained in each miniature reactor;
  a mobile sensor holder able to receive at least an external sensor, the mobile sensor holder comprising sensor moving means for moving the external sensor from a miniature reactor to another one and for allowing for the real time measurement of said at least one optical property; and
  monitoring and processing means for receiving in real time measurements of the optical property from one or more external sensors and for monitoring in real time a motion of the mobile sensor holder.

The invention also relates to a method for automatically measuring at least one optical property of cell cultures contained within a miniature reactor battery, comprising the following steps of:
  measuring automatically at least one optical property of a culture contained within one of the miniature reactors via an external sensor;
  moving in a robotized way the external sensor towards another miniature reactor; and
  measuring automatically at least one optical property of a culture contained within another miniature reactor through the external sensor.

DEFINITIONS

The expression "miniature reactors" means a fermentor, the useful culture volume of which ranges from at least 2 ml up to a maximum of 500 ml. More specifically, it is meant under "mini-reactors" such fermentors having their useful culture volume ranging from 60 ml to 500 ml and it is meant by "micro-reactors" such fermentors having their useful volume ranging from 2 ml to 60 ml.

It is meant under "cell culture" a micro-organism culture, such as bacteria, yeasts, fungi and any other eukaryotic cells.

It is meant under "Vref" the nominal voltage established across the receiving diode of the turbidity sensor, the value of such a parameter determining the sensitivity of the Ve measurement.

It is meant under "Ve" the voltage measured across the emitting diode of the turbidity sensor, such a value being a function of the culture turbidity.

It is meant under "DO" the optical density as measured by a spectrometer.

BRIEF DESCRIPTION OF THE DRAWINGS

FIG. 1 shows a front view of a cell culture platform comprising a micro-fermentor battery, systems for regulating the temperature by Peltier effect, an external sensor arranged on a mobile sensor holder, and acquisition and monitoring electronic modules, according to a preferred embodiment of the present invention.

FIGS. 9A and 9B respectively show front and side views of a micro-fermentor inserted into its thermostatic support of the Peltier type, according to a preferred embodiment of the present invention.

FIGS. 14A, 14B and 14C respectively show sectional views of an injecting and sampling system in high and low positions, as well as a front view of a piston according to the present invention.

FIGS. 14D, 14E, 14F, 14G and 14H show sectional views of a purging device in various positions according to the present invention.

DETAILED DESCRIPTION OF THE INVENTION

Figure 2A:
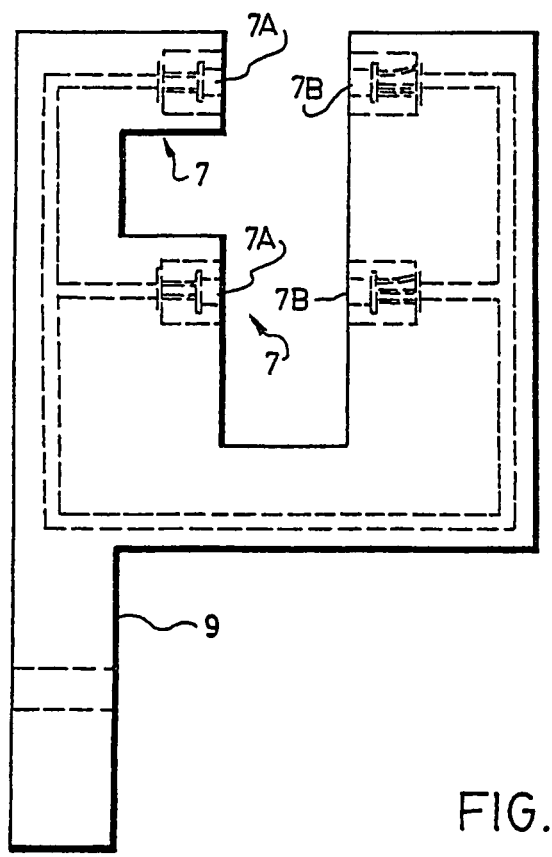
FIGS. 2A, 2B and 2C respectively show sectional, top and side schematic views of a mobile sensor holder, according to a preferred embodiment of the present invention.
Figure 2B:
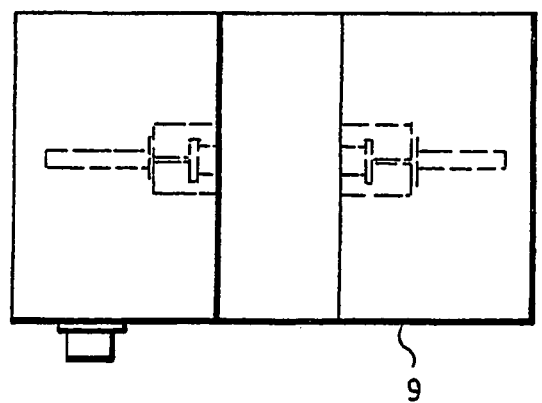
Figure 2C:
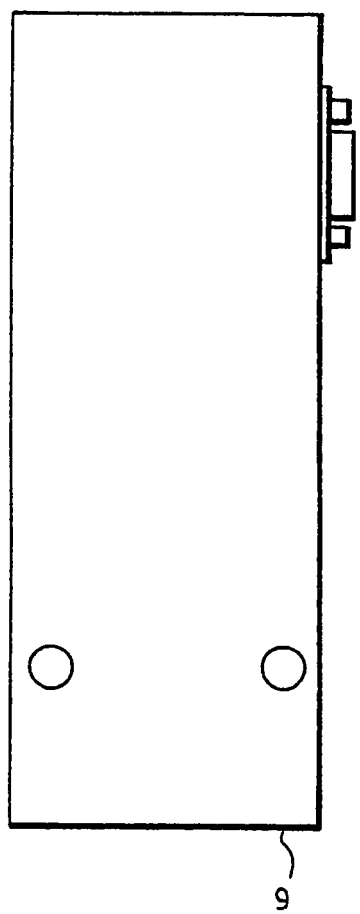
Figure 2D:
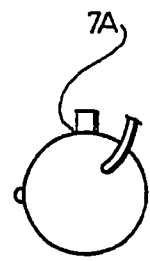
FIGS. 2D, 2E, 2F and 2G respectively show back, side and front views of an emitting diode, as well as a back view of a receiving diode used to measure the turbidity, according to a preferred embodiment of the present invention.
Figure 2E:
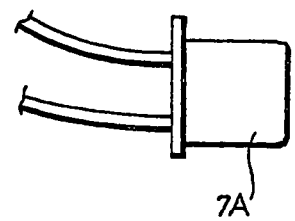
Figure 2F:
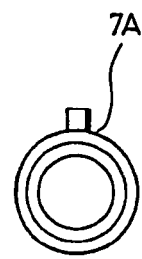
Figure 2G:
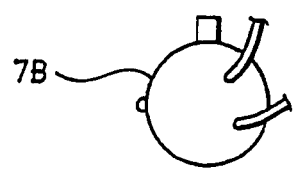

FIG. 1 shows a cell culture platform 1 according to a preferred embodiment of the present invention. The platform 1 lies on the original concept of the miniaturization and automation of microbial cultures, with a low volume (60 ml), achieved in micro-fermentors 3. Preferably, the platform 1 comprises a battery of eight micro-fermentors 3, but such a number might vary depending on the applications or the needs, as well as the volume of each micro-fermentor 3.

The body of the micro-fermentors 3 can be made of reactors manufactured in glass tubes 5 (see FIGS. 9A and 9B) with a 2 cm square section, being 16 to 18 cm high, provided with headers connected to pipes allowing for the flow of liquid and gas fluids. The glass tubes 5 should normally be sterilized before each new use. Such glass tubes could also be replaced by ready to use, one-way plastic sterile reactors, for example, in polycarbonate.

The micro-fermentors 3 are assembled in batteries within a compact and ergonomic system with an integrated supervision of the culture achievement. As will be explained below, because of their level of sensor equipment and their automation extent, such micro-fermentors 3 offer the same potentialities as large volume laboratory fermentors.

One or More Sensors Arranged in a Mobile Sensor Holder

In the known first generation battery system from the prior art, each micro-fermentor is arranged in a metal block in which a pair of emitting and receiving diodes is inserted. Such diodes are satisfactory as far as performance is concerned (wide turbidity ranges, arrangement externally to the fermentors, low cost, etc.). However, each culture block is provided with its own sensor comprising a particular pair of diodes. It has been found difficult to accurately calibrate such sensors the ones relative to the others. For example, out of 100 LED diodes or Darlington receptors, only 10% are found to be useful, showing comparable response dynamics. Moreover, it has been found that coupling the LED and Darlington diode pairs for each sensor led to related, although not identical, response dynamics. Using a gain setting potentiometer could allow to standardize the various pairs for a given DO (for example 1), but not on the whole measurement range (for example, from DO 0.5 to DO 100 for a High Optical Density (HOD) culture). Thus, the response curves of the various sensors as a function of the turbidity (DO) of a culture or a cell suspension were not able to be superimposed. Thus, for automatically converting the Ve measured values and in order to display them in DO units, there should have been introduced in the programmes as many modelling equations relating Ve to DO as sensors being used, which was not acceptable.

The platform 1 according to the present invention offers a solution to such a problem relying on the original concept of one single and identical external and mobile sensor 7 being used for the sequential measurement of an optical property of a cell culture battery achieved in micro-fermentors 3, by means of a mobile sensor holder 9 driven by a stepper motor 8, under the control of a computer programme.

In particular, the sensor 7 allows for a direct and in line measurement of the turbidity of the whole pending cultures in the various micro-fermentors 3. The turbidity-measuring sensor 7 is arranged in a mobile sensor holder 9 being moved by means of a motor on a linear axis along a row of micro-fermentors 3 and allows to sequentially measure, with accuracy and reproducibility, the turbidity in each of the micro-fermentors 3 without the operator being involved on the pending cultures.

Positioning the sensor holder 9 using the stepper motor 9 could occur with a resolution in the order of approximately 10 to 100 μm according to the moving mechanism being used, with a very high reliability. It is therefore possible to perform several readings successively on a single micro-fermentor 3. It is to be noted that, instead of a stepper motor, variations would be to use a circular arm (servo-motor) or a robot arm or any other system allowing for the relative movement between the sensor 7 and the micro-fermentors 3.

Figure 7:
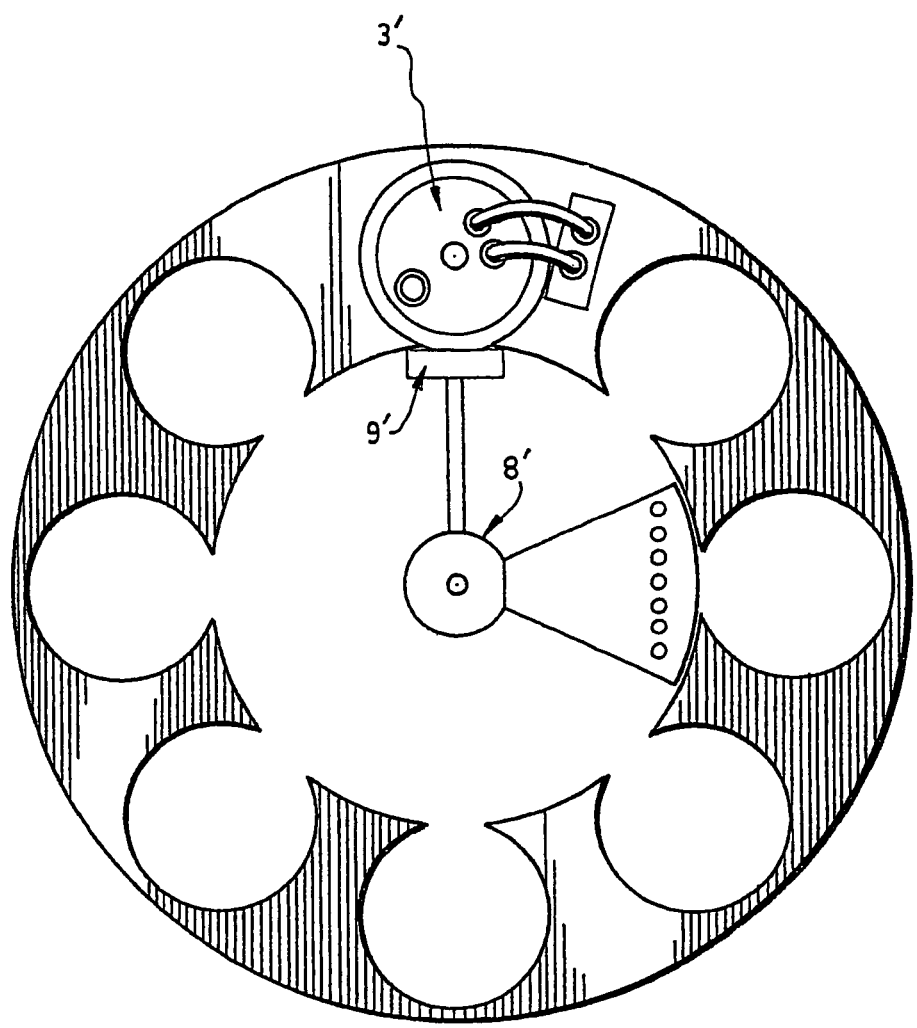
FIG. 7 shows a bottom view of a 250 ml mini-reactor battery provided with a mobile arm providing a circular movement, for measuring the turbidity in reactors, according to a preferred embodiment of the present invention.

Referring to FIG. 7, there is illustrated a particular alternative of the mobile sensor holder 9' connected with a motor 8' allowing it to run according to a circular movement in front of mini-fermentors 3' where cell cultures are being made.

Preferably, as shown in FIG. 2A, the turbidity sensor 7 consists in at least one optical component pair: an infrared light emitting diode 7a and a Photodarlington receptor 7b for receiving the residual transmitted light having passed through the micro-fermentor 3. There is also illustrated that more than one sensor 7 could be arranged on the sensor holder 9. Inserting two pairs of diodes 7 offers the possibility to perform a measurement at different heights of the culture reactor.

Figure 3:
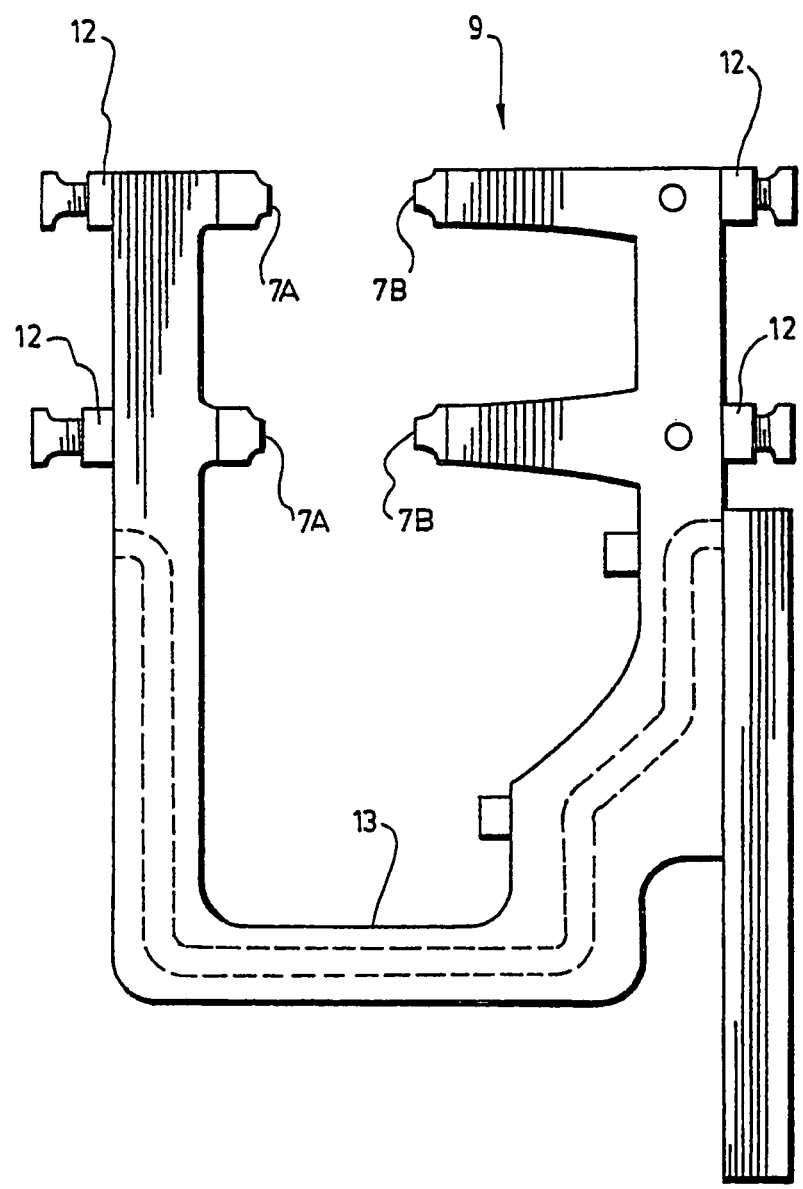
FIG. 3 shows a side view of a fork-shaped sensor holder intended to be arranged on a guiding system for a cell culture platform, according to a preferred embodiment of the present invention.
Figure 4:
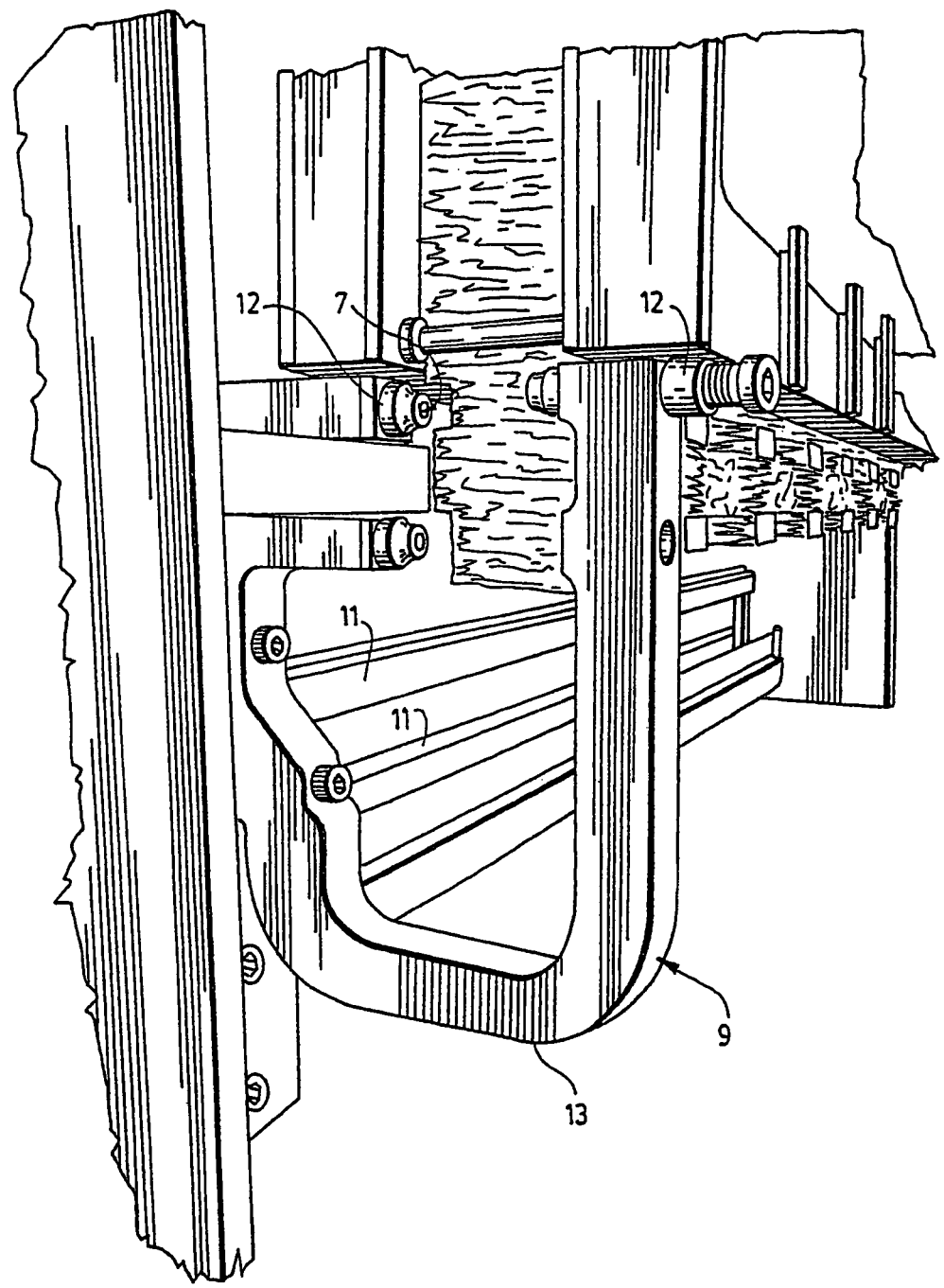
FIG. 4 shows a perspective view of a sensor holder arranged on two rails of a micro-organism culture platform, according to a preferred embodiment of the present invention.
Figure 5:
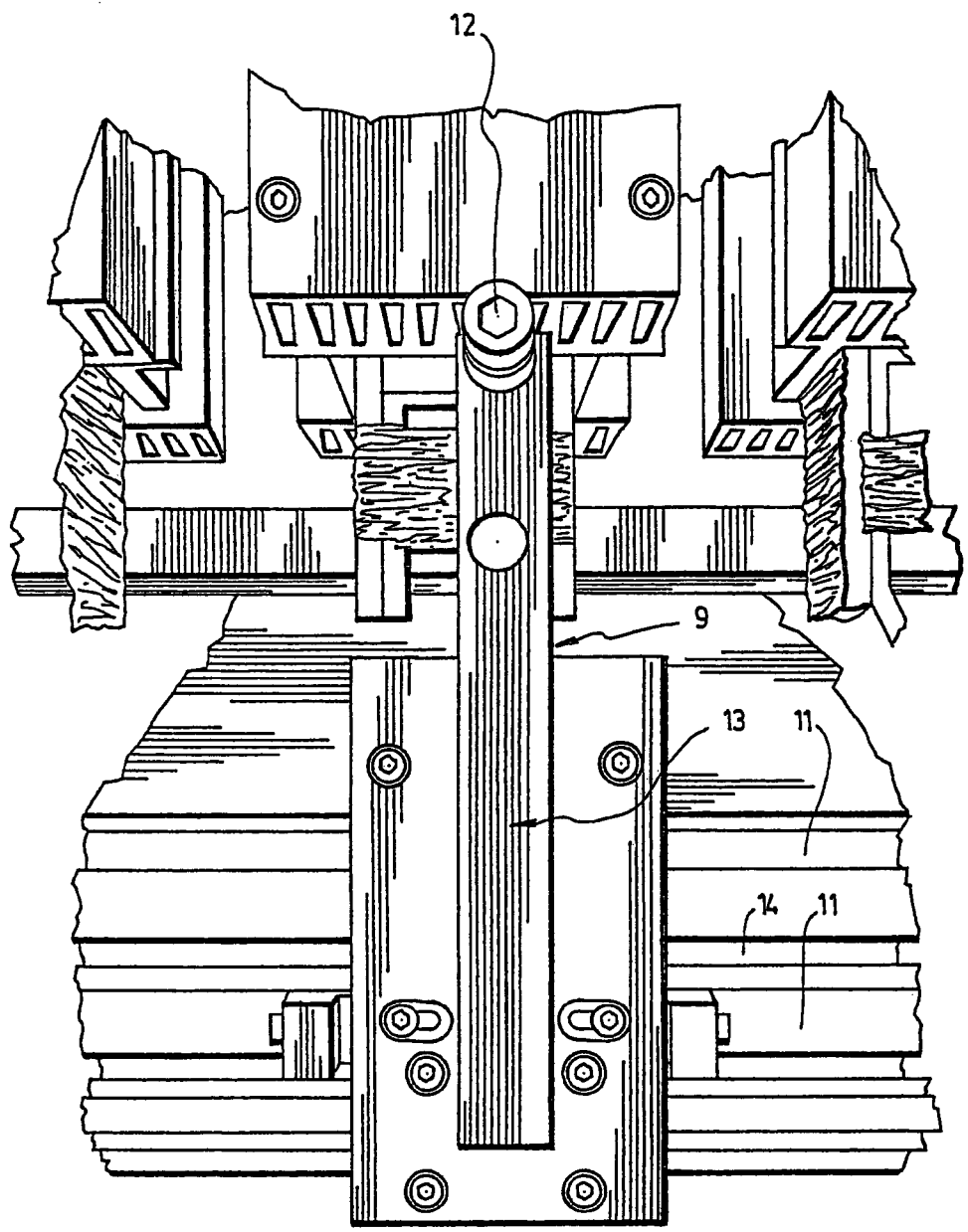
FIG. 5 shows a front view of the sensor holder illustrated in FIG. 4.
Figure 6:
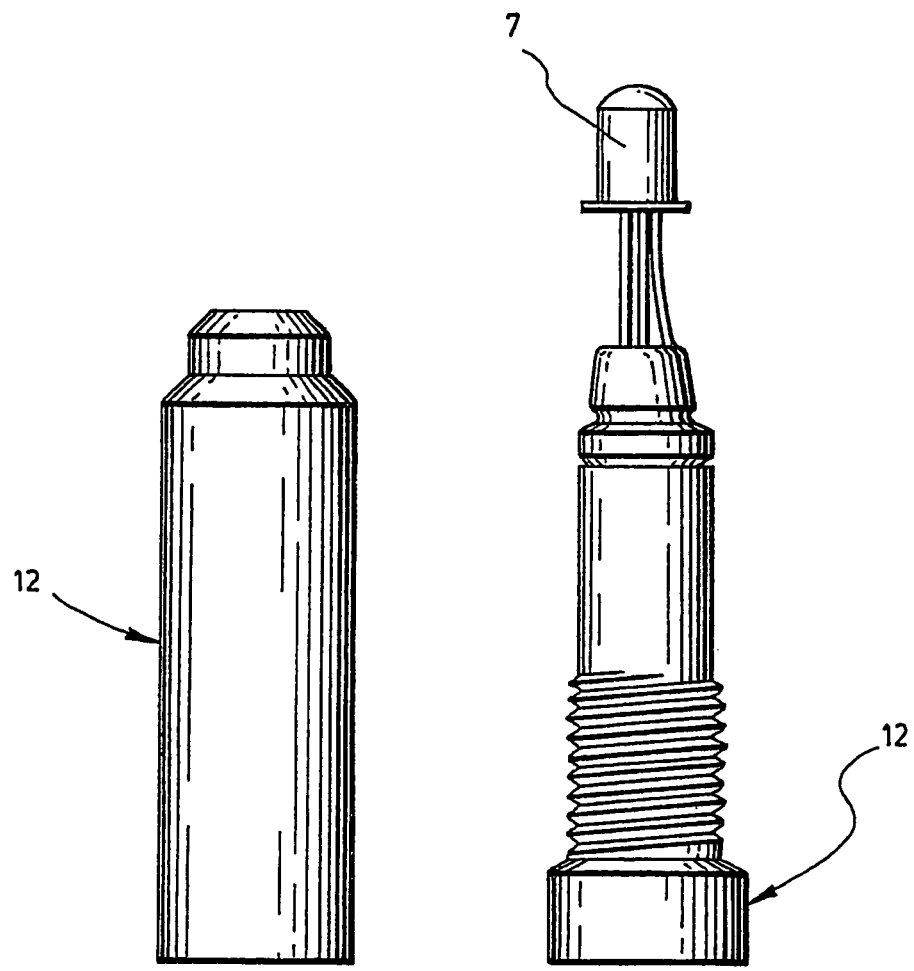
FIG. 6 shows a side view of an element of the turbidity sensor showing in detail the support for an arrangement on the sensor holder as illustrated in FIG. 4, according to a preferred embodiment of the present invention.

As illustrated in FIGS. 3 to 5, the pairs of diodes 7 may be fixed on a sensor holder 9 with an integral fork shape 13 having two mobile carriages moving along two rails 11 under the action of a notched belt driven by a stepper motor. In such a case, the sensor holder 9 is provided with mobile diode supports 12 (see also FIG. 6), thus facilitating inserting and changing the diodes 7, depending on the needs. Having available a fork or yoke-shaped sensor holder 9, the shape and the sides of which could be modified, allows to secure on it different sensors, either available on the market or new, and thus to increase the analysis possibilities of microbial cultures, for example, using multiple turbidity sensors at various heights. In other cases, such a device could open the way to decantation and flocculation studies for microbial strains or adherence in the reactor, or for developing methods, or for evolution or enrichment studies of strains, by means of cyclic cultures.

Figure 8:
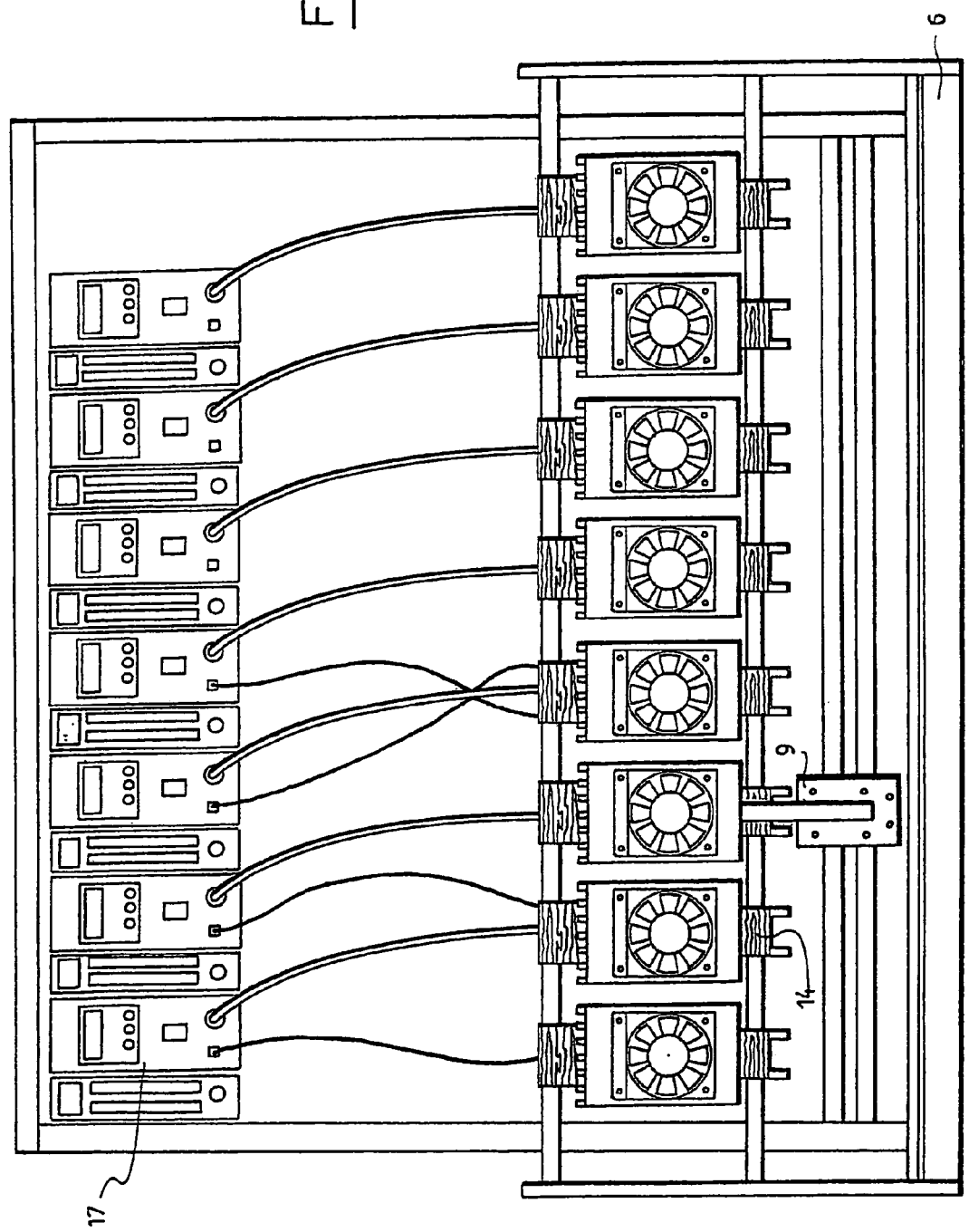
FIG. 8 shows a front view of a cell culture platform provided with thermal regulation blocks by Peltier effect, according to a preferred embodiment of the present invention.
Figure 10:
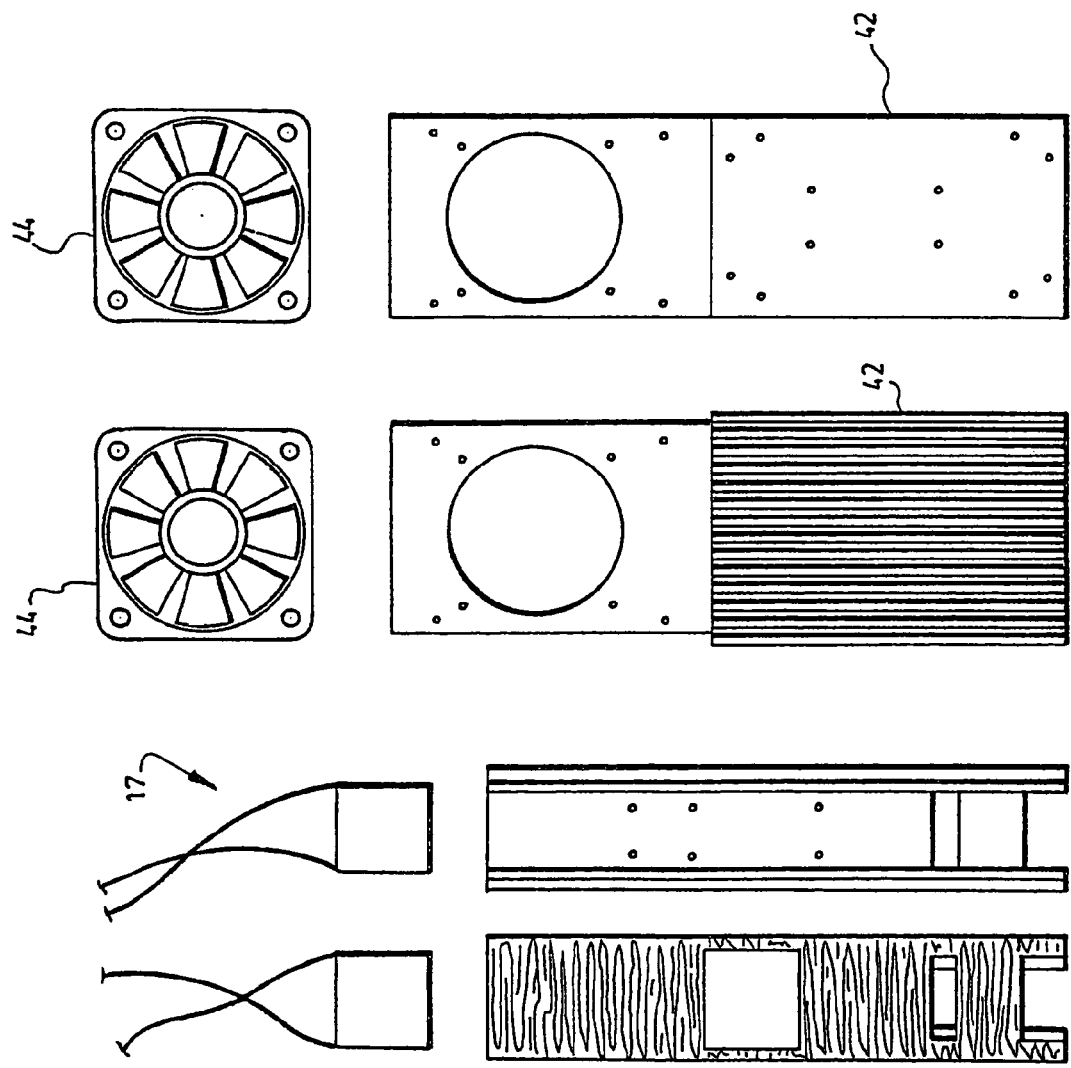
FIG. 10 shows a plan view of elements constituting a Peltier type thermostatic reactor support, according to a preferred embodiment of the present invention.

The sensor holder 9 is preferably provided with two sliders or guides being shifted to the back so as to protect the mobile parts from splashes or possible leakages. A retention compartment 6 (see FIG. 8) could be arranged under the battery, should the culture leaks, in the case of a micro-fermentor 3 being broken, for example. The guiding mode via parallel rails significantly eliminates vibrations and allows for reducing the distance between the optical components and the walls of the micro-fermentors 3, so reducing the light beam spreading. A measurement window 14 located in the supporting block allows for an optical measurement at half-height of the micro-fermentor 3. The bottom of the micro-fermentor 3 is also available for a second sensor. Various micro-fermentor designs can be used depending on the application type.

The sensor holder 9 may also be adapted in order to accept optical fibres or other types of sensors (bioluminescence—for example, for producing recombinant proteins, phosphorescence, colorimetry, fluorescence, etc.).

In particular, a light sensor (photomultiplier (MP)) can also be used for studying the expression of reporting genes, such as the lux gene. Such a luminescence sensor can be arranged on the same mobile sensor holder 9, already provided with a sensor for measuring the turbidity 7.

It should be noted that such light sensors are very expensive (1000 euro for the only PM) and require a complex standardization. According to the old concept, there should be arranged a sensor at the level of each micro-fermentor. On the other hand, using one single mobile sensor holder passing before the micro-fermentors decreases, for example, by 8 the equipment costs of a 8 micro-fermentor battery.

Obviously, various geometries of the mobile sensor holder 9 can also be contemplated. The modification of the sensor holder 9 makes it possible to adapt the measurement system to the reactor geometry, depending on the needs, whether these are tubes with multiple 60 ml micro-fermentors, or 2 to 5 ml tubes, as well as 250 to 500 ml mini-reactors. Similarly, it is possible to select accurately the reading angles and distances.

Figure 11:
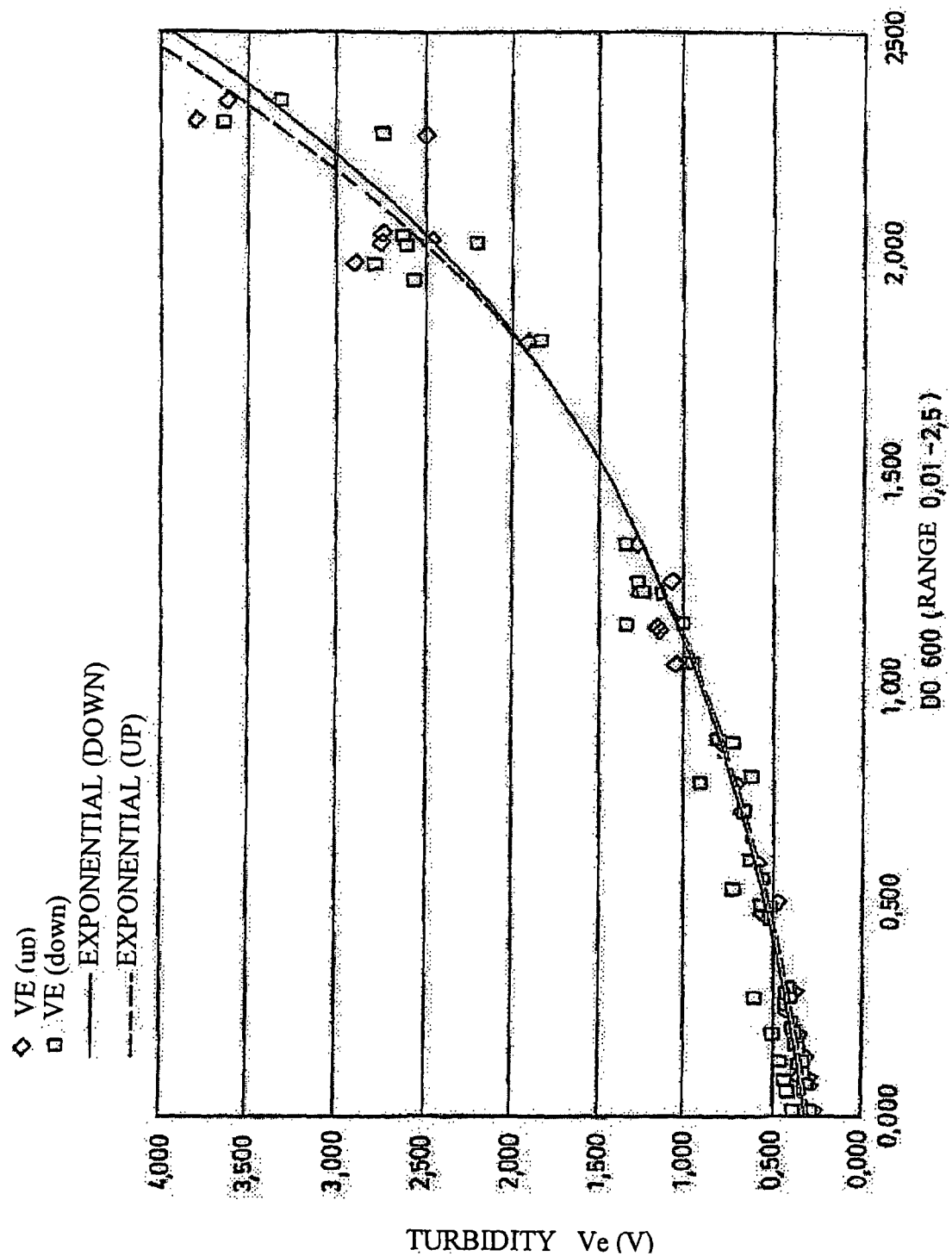
FIG. 11 shows the curve relating the evolution of the turbidity measurement to the manual measurement of the DO for cultures achieved in parallel with 7 micro-fermentors and one *E. coli* strain.
Figure 12:
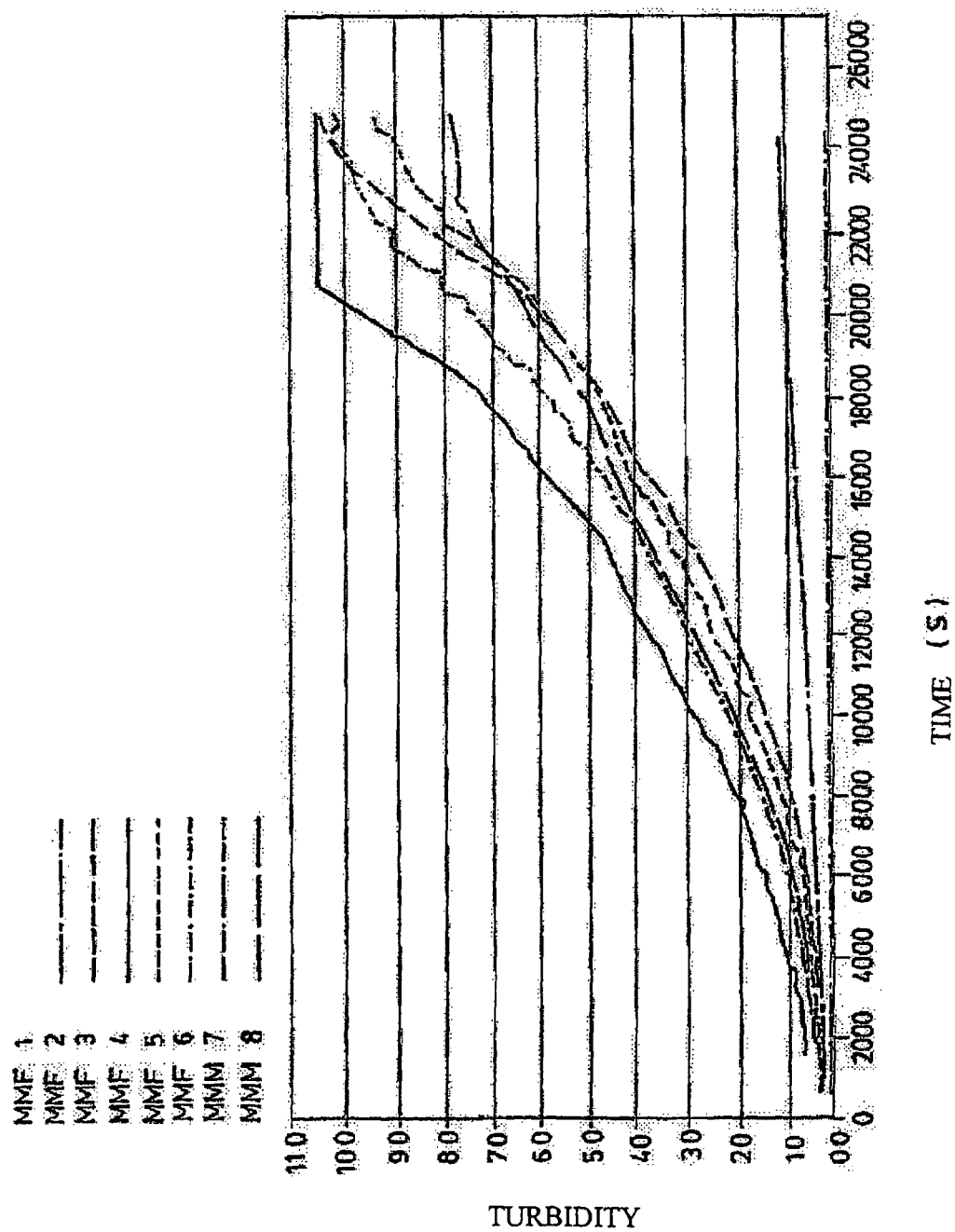
FIG. 12 shows a graphical interface of a monitoring programme for the system according to the invention, showing, inter alia, evolution curves of the turbidity as a function of time in each of the micro-fermentors.
Figure 13:
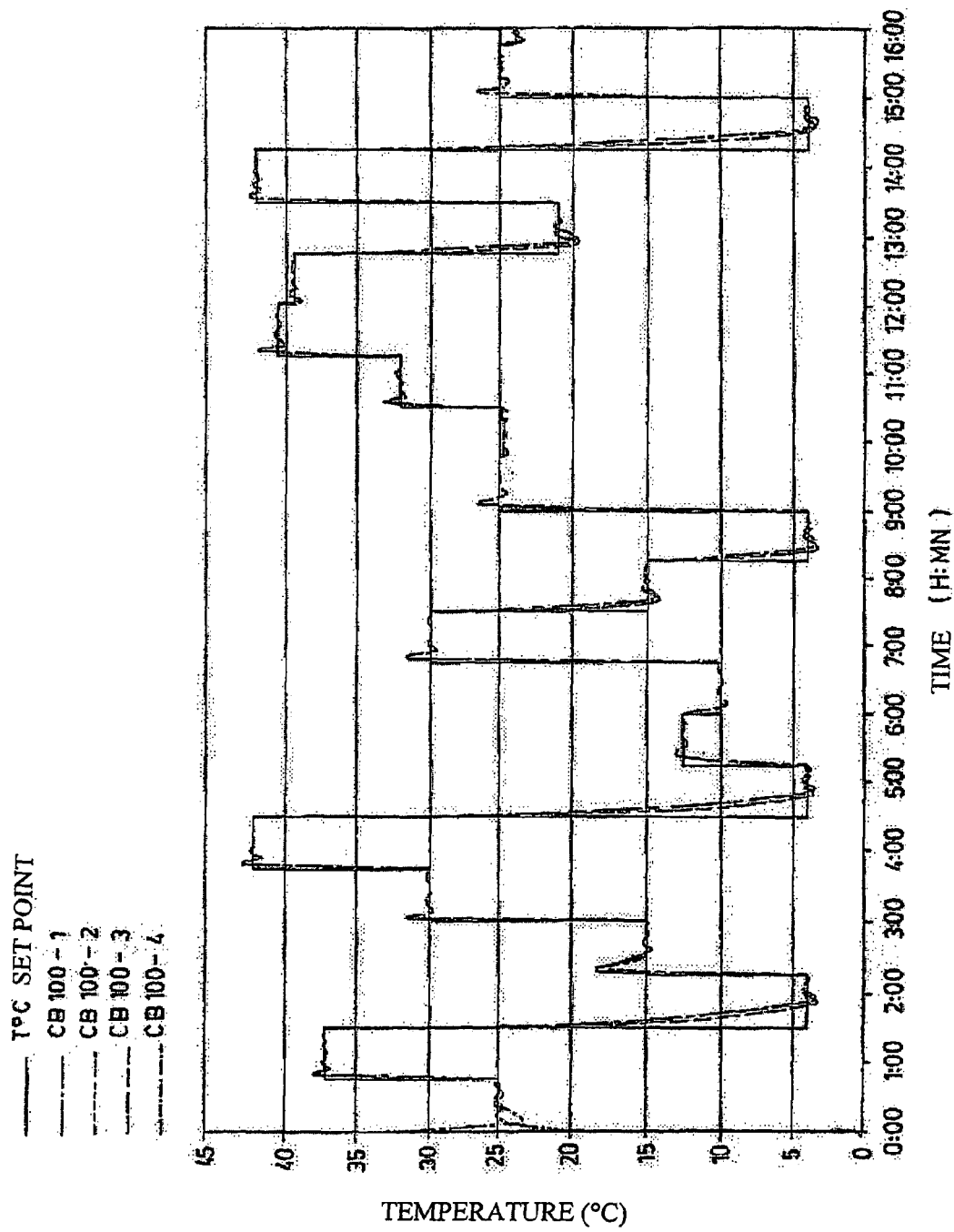
FIG. 13 shows temperature curves as a function of the set point and the time for four thermal regulators, according to a preferred embodiment of the present invention.

Turning to FIG. 11, there is shown the evolution of the Ve voltage measured across the emitting diode 7a as a function of the turbidity of a culture. Referring to FIG. 12, there is shown the evolution of the Ve voltage across the emitting diode 7a as a function of time. This way, the cell concentration can be determined of a culture in each micro-fermentor 3 (concentration expressed in DO units for example). The equation relating Ve to the DO, introduced in the monitoring programme, allows for getting in line the value of the latter. Such a device allows for a measurement of the turbidity in various sensitivity ranges, corresponding to DO with 0.05 to more than 100 DO units (for the *Escherichia coli* model bacterium) and 0.05 to more than 300 for the *Saccharomyces cerevisiae* model yeast. It allows for working with minimum or complex media.

The sequences of the sensor holder 9 shift and the turbidity measurement are supervised by the computer programme. Depending on the selected sensitivity (Vref value) for the measurement to be performed, it is possible to measure turbidity corresponding to a range of optical densities ranging from 0.05 to 100 (for *E. coli*).

The sequences of the sensor holder 9 shift and the turbidity reading are the main loop of the computer programme being used (Institut Pasteur 2002 deposit). The latter is based on a configuration file describing the type of material being used and the operating mode. Thus, the computer programme can be adapted to various motorization solutions. For moving the sensor holder 9, a stepper motor 8 has been chosen (SANYO DENKY 103H71260440 type) working in an opened loop and in a micro-step mode ($\frac{1}{8}^{th}$ of step for a resolution of 200 steps/rotation). The monitoring board (PCI-7344, National Instruments) arranged in the computer may pilot four independent axis systems or coordinates. A connecting box (UMI-7764, National Instruments) connects the motor control board with the power board (SANYO DENKI). For a silent and fast operation, a transmission via a notched belt has been elected. Two switches bound the shifting area (650 mm for 8 micro-fermentors). The final linear resolution is 80 micrometers for a carriage speed of 42.6 cm/sec. Under the control of the computer software, the sensor holder 9 module is sequentially positioned in front of each active micro-fermentor 3 for the period of time required for the various measurement operations. The frequency of such a loop as well as the time between two shifts are defined by the user.

As any optical device, it is necessary to periodically check the response from the sensor 7 depending on the turbidity. For this, one or more standard tubes, containing turbid products (as formazin), cell suspensions or opaque substances, with a given turbidity, are arranged in the appropriate locations of the battery. At the beginning of a trial, or during handling, the programme automatically performs the successive reading of such tubes for calibrating the sensor: either in NTU units (Nephelometric Turbidity Units), or in Optical Density units, or in relative opacity units. Thus, calibrating the sensors 7 occurs automatically and eliminates any uncertainty regarding the stability or the possible drifts, which is a particularly severe problem when comparing strains or methods.

The platform 1 according to the invention allows for ensuring the standardization of cultures as the present method is the only one to offer a direct, sequential and in line measurement of the turbidity of all the processed cultures by a running or scrolling measurement single cell. The system also allows for recognizing and comparing in real time the growth phase of all the cultures achieved in parallel.

The system according to the invention allows to achieve cultures in reactors with variable volumes making use of the same automation and standardization functionalities as the cultures in 60 ml tubes, for example, the differential supply of $O_2$ and the introduction of the programmed DO inducer.

In particular, the present system allows for very low volume automated cultures for selecting new molecules for therapeutic use, directed against bacterial strains maintained in optimum growth or in conditions as predefined by the research worker. Such cultures are achieved in aerated tubes (2 to 5 ml), supported on racks, with an in line measurement of the turbidity by the scrolling sensor and a programmed injection of any molecule being cultured.

The present system also allows for automated cultures (250 to 500 ml) of cylindrical mini-reactors, showing at an appropriate height an excrescence with two parallel faces and two oblong faces allowing for the easy flow of the culture medium driven by a stirring system. The scrolling sensor successively passes before the excrescences of the mini-fermentors of the battery and is positioned at the level of the two parallel faces for a correct reading. In the approach of systematic studies of the proteins coded by genes of sequenced genomes, numerous proteins only express very weakly. Such proteins are toxic for the bacterial strains hosting the corresponding genes, or have biochemical and functional characteristics (membrane proteins) little favourable to the expression under a soluble form. Increasing the culture volumes, coupled with the advantages from the automation, should allow to compensate for such low expression levels and to thereby meet the expectations from the functionality studies of such proteins. Such a technology could also be applied to the optimization of methods that are to be transferred to high production scales.

The platform 1 according to the present invention avoids implanting bulky sensors within the reactors. Locating outside the reactor one or more sensors allows for reducing the reactor size with no decrease of the useful volume. This allows for obtaining smaller batteries able to be easily implanted in laboratories. Using such batteries is also compatible with the interior of a Microbiological Safety Station (PSM).

Another advantage associated with the system according to the present invention is that the availability, at any time, of the culture turbidity as well as the history of its evolution, allows to trigger events associated to the cell amount and to the growth rate, such as, for example, the additions of culture media or inducer solutions (via the injecting/sampling automat which will further detailed below). Similarly, the $O_2$ concentration can be increased, the temperature modified and samplings made. Similarly, the pH can be regulated. The present platform thus allows for a very important increase of the monitoring possibilities of the cultures and the analysis performance.

The platform 1 according to the present invention allows for a cost reduction, while integrating the best optics for improving the sensors. It allows to integrate particular optics (optic fibres, spectra, high power sensors, etc.) and the cost is divided by more than n times the number of reactors being used.

Moreover, the sensors 7 being outside the culture tube do not need to be sterilized, this being an additional constraint for the existing internal sensors.

Using a mobile sensor according to the invention therefore solves the major problem of the invention as disclosed in the Application WO 99/27349, i.e. the calibration difficulty of multiple static sensors which are dedicated to their own micro-fermentors. The sensor 7 according to the present invention through the standardization of the in line calibration during handling makes the turbidity measurement reliable and reproducible, thereby allowing for the perfect comparison of the turbidity of cultures conducted in parallel. In addition, the cost is decreased and it is possible to adapt other sensors (such as the bioluminescence one) on the sensor holder.

The scrolling sensor 7, as described hereinabove, integrated into the platform 1 allows for having efficient equipment in the field of the parallel automated micro-cultures. In addition to the Genomics and Proteomics, numerous other applications are possible:
  a comparison of strains in microbial physiology;
  a development of culture media;
  a study of the simultaneous effects of the environmental multiparametric factors (predictive microbiology). Case of hard to cultivate strains (high latency and generation time);
  an optimization of the culture methods; scale-up;
  a study of biofilms;
  a depollution (decantation study; enrichment of strains, mixed cultures);
  a screening of strains;
  a screening of compounds of pharmaceutical interest;
  biotransformations; and
  a cell therapy; physiological condition.

The application areas cover numerous fields:
  food processing industry;
  pharmaceutical industry;
  clinical microbiology;
  environment (biofilms, polluting agents), depollution and treatments;
  fermentation laboratories and industries; and
  research.

As an example, is described below a major application in the field of biotechnology, i.e. a study of biofilms.

One of the main causes for nosocomial diseases (10,000 deaths per year in France) is the formation of bacterial biofilms and yeasts on catheters and various medical or surgical implants. In order to develop anti-biofilm therapeutic strategies, it is necessary, on the one hand, to study the development of such biofilms and to find drugs able to modify their formation kinetics and, on the other hand, to characterize the plastics and other materials on which the microbial adherence is decreased or even removed. The micro-fermentors with the continuous measurement of the turbidity and the accurate and reproducible knowledge of the growth phase are perfectly well appropriate for such a study. In particular, the scrolling sensor can play an essential part.

In the following simplified example, it is desired to observe the anti-adherent properties of plastics of various natures, for example, Nylon, Teflon, PVC, polycarbonate, etc. In the micro-fermentor tubes are introduced small strips of various plastics, such that their faces are perpendicular to the light beam of the turbidity sensor. The culture is seeded with a hyperadhesive microbial strain. The growth occurs and the strain adheres to the various strips with a particular kinetics associated to the nature of the plastic. The scrolling sensor is programmed so as to accurately position, at programmed time intervals, in front of the different strips. The measured turbidity differences allow for inferring the sensitivity of such plastics. Another complementary trial could be to add antibiotics and observe the disappearance of the biofilms according to the materials and their thicknesses. In order to take into consideration the adherence on the fermentor itself, an arrangement could consist in measuring the turbidity through the fermentor by inserting into it 0, 1 or 2 glass laminae. The resulting equations would allow for knowing the biofilm thickness on the fermentor itself and the turbidity of the suspended cells. Another arrangement could consist in using a tube having areas with various width, thus with different optical paths. Another means could consist in treating the fermentor to make its internal surface non adherent.

In a similar approach, it could be possible to determine the decantation rates of the microbial cultures and to develop flocculating mutant enrichment systems, automatically emptying the cultures at a certain rate and then adding fresh medium (cyclic cultures).

Another way to analyse microbial cultures could consist in measuring the turbidities at different wavelengths and treating the resulting equations, with their coefficients being a function of the cell size.

The invention could therefore be found to be an important tool in the fields of chemistry and environment for the same reasons of cost decrease, analytic power increase through the use of multi-sensors, increase of the measurement reliability, automation of the measurements and in line computer processing.

The present automated culture platform currently uses glass reactors that are to be conditioned and autoclaved before each new use. Similarly, the introduction of sterile medium in the reactors occurs under a bacteriological hood. Such constraints can be perceived as disadvantages in a sense of a waste of time between each culture cycle, whereas such culture cycles are fully automated. An in line sterilization system for the reactors could therefore be contemplated, coupled with an automated introduction of culture medium. On the other hand, developing ready to use and one-way polycarbonate sterile reactors could be contemplated.

Either one of these two solutions should enhance the automated and, in the long run, robotized dimension of the suggested technology.

Monitoring and Independent Regulation of the Temperature for each Culture

The regulation of the growth temperature is an essential parameter in performing a microbial culture. The platform 1 according to the invention comprises therefore a temperature regulating system 17 (see FIG. 8). Such a regulation for all the micro-fermentors 3 of the battery could preferably be a regulation of the temperature by Peltier effect, being independent and programmable for each micro-fermentor 3 (range from −5 to 80° C.).

The Peltier effect system 17 which is illustrated in FIGS. 8, 9A, 9B and 10 comprises thermal dissipators 42 provided with fans 44.

Monitoring the temperature is effected by autonomous and independent PID regulators (Derived Integral Proportional), coupled to Peltier effect modules. The set temperatures (O to 65° C.) and those measured by the Pt100 probes are transmitted via a RS-485 link between the thermal modules and the computer.

The possibility to programme the culture temperatures is a key factor in the optimisation of bacteriological methods. The possibility to automatically set the temperature, or to perform temperature increments, allows for the production of proteins to be optimized under a soluble form, performing for example low temperature cultures. The independent programming of such a parameter for each reactor allows, depending on the bacterial strain to be cultivated, or according to the specific sequence of the gene to be expressed, to choose the most favourable temperature for the growth or the expression of recombinant proteins.

Automation of Injecting and Sampling Operations in the Course of Processes

Figure 14E:
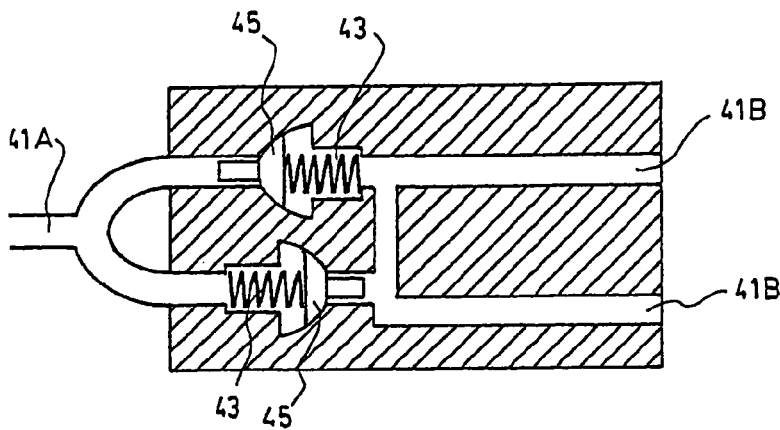

As illustrated in FIGS. 14A, and 14B, an injecting/sampling automat 15 is integrated into the micro-fermentor 3 culture platform 1. It allows, depending on a value of the turbidity measured in real time or of time or any other parameter measured in the reactor, and predefined by an operator, to inject automatically one or more products (substrates, inducer). The injecting/sampling automat 15 can operate synchronously with the sensor 7 for the in line measurement of the turbidity and ensures the automatic introduction of the inducer at the culture phase corresponding to the turbidity value as programmed by the user. In addition, in the case where it is necessary to follow the expression kinetics of proteins, such an automat 15 allows to perform samplings of variable volumes on all the cultures being processed and to store them at 4° C. Each operation is supervised by the computer programme managing the whole platform tasks.

As explained earlier, the platform 1 comprises a temperature regulated support by means of Peltier effect modules able to maintain a set temperature of 4° C. Such a support accepts removable blocks (350×25 mm for example) perforated with 20 to 24 holes able to receive small 12×32 mm vials, with a 0.2 ml to 2 ml maximum capacity. Blocks adapted to various size vials can be integrated into the support. In such a case, the blocks comprise identification elements allowing the piloting system of the support to automatically adapt itself.

A storing area overlies one of the support ends and protects removable needle supports 19 the number of which depends on the number of reactors being used. Such a storing area is provided with small heating resistors serving to sterilize the end of the needles and a header for draining possible liquid splashes.

The needle supports 19 are placed on motorized up-down modules secured on a mobile guide circulating along two parallel rails. Such a mobile guide is interdependent with a notched belt driven by a stepper motor under computer control. It is understood that the mobile guide can be interdependent with the previously described sensor holder 9. Indeed, it is possible to have mobile guides for the needle supports 19 being preferably independent from the sensor-holder 9 containing the turbidity sensor.

The needle supports 19 are removable and arranged on the automat depending on the number of paths being used. It is the function of the computer control to identify the number and the position of the needle supports 19 as well as the type of blocks for vials 33 and to suggest to the user a restricted and adapted selection of actions. In order to extend the use possibilities, it could be interesting to use two (2) shifting systems able each to manage four (4) needle supports.

As illustrated in FIG. 14A, a needle support 19 comprises 4 main elements:

a pressing roller 23 crushing a flexible pipe 25 via two springs 27;
a spring 31 return mobile piston 29, the lower part of which consists of a head allowing for centring and maintaining the neck of the vial 33 during the operation, and a notch 32 at the higher end to lift the pressing mechanism 23 and allow the fluid to be circulated;
a reinforced needle 35 connected with the flexible pipe 25; and
a purging channel 37 having one end, parallel to the needle, used for transmitting "pneumatic information" retrieved by the purging device 39.

The purging device 39 comprises a 4-path circuit, two of which are connected with the reactor by a capillary tube 41A and each provided with a counter-pressure spring 43 and a rubber valve 45 arranged in opposite positions. The two other paths 41B are connected with the needle support 19 by two capillary tubes. The dead volume thus simply depends on the distance between the reactor and the purging device and the internal diameter of the capillary element used for connecting them. The purging device 39 does not need any additional control. It can be sterilized.

Through pressurized or vacuum vials 33, it can be avoided to have to make use of solenoids or pumps. It is easy to find on the market low volume sterile and vacuum vials. For the transfers under pressure, the solute and the air volume needed for the compression will be injected with a thin needle through a specific cork with variable thickness, in an already sealed and sterile vial.

Another solution would be to use a encapsulated tube with the bottom being replaced by a tight cork withstanding a needle prick. The overpressure in the micro-fermentor 3 being very low, the internal pressure needed in the vial 33 should not exceed 0.5 to 1 bar.

The needle support 19 being integral with one same mobile guide, the automat can only perform one operation at a time. The monitoring programme is to indicate to it with which needle and on which vial it has to operate, and memorize the waiting events in a "first in-first out" stack. Considering that the duration of a cycle is 15 seconds at the most, the waiting time between the operation request and the execution thereof would be 2 minutes at a maximum (case of 8 micro-fermentors), which is largely sufficient at the scale of a bacterial culture.

A standard cycle comprises the following actions:
the mobile guide accurately positions the needle support modules 19 vertically to the selected vial 33. The up-down module drives the corresponding needle support 19 towards the vial 33 for transfer operations; and
the needle 35 goes through the rubber cork of the vial 33 and the needle support 19 reaches its predefined low position. Upon contact with the neck of the vial 33, the piston 29 lifts and temporarily releases the pressing roller 23 inside the needle support 19. The end of the purging channel 37 is plugged by a firm contact with the cork 28 of the vial 33 (but without perforating it).

If the vial 33 is pressurized and contains a solution to be transferred into the reactor:
transferring the liquid occurs through the outlet (OUT) of the purging device 39 as the IN path can only close under pressure (see FIG. 14H); and
the excess pressurized gas volume is sufficient to purge the capillary tube.

Figure 14F:
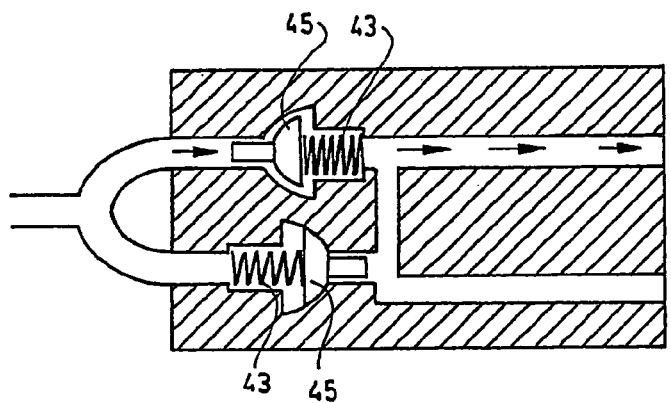
Figure 14G:
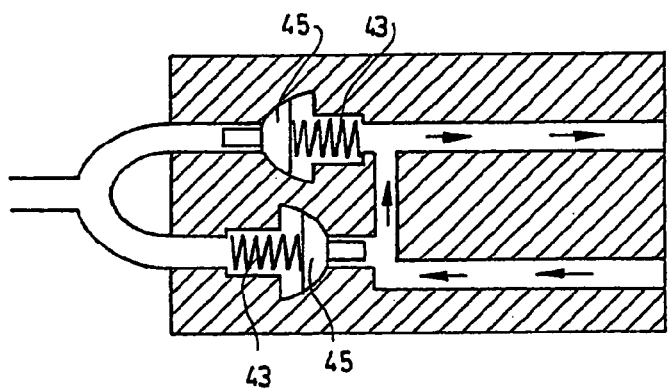
Figure 14H:
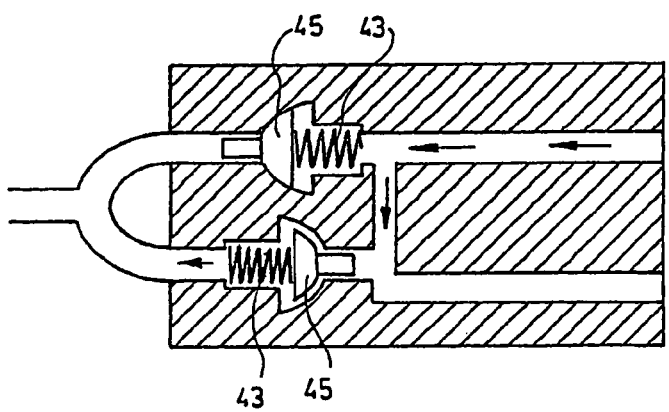
Figure 15:
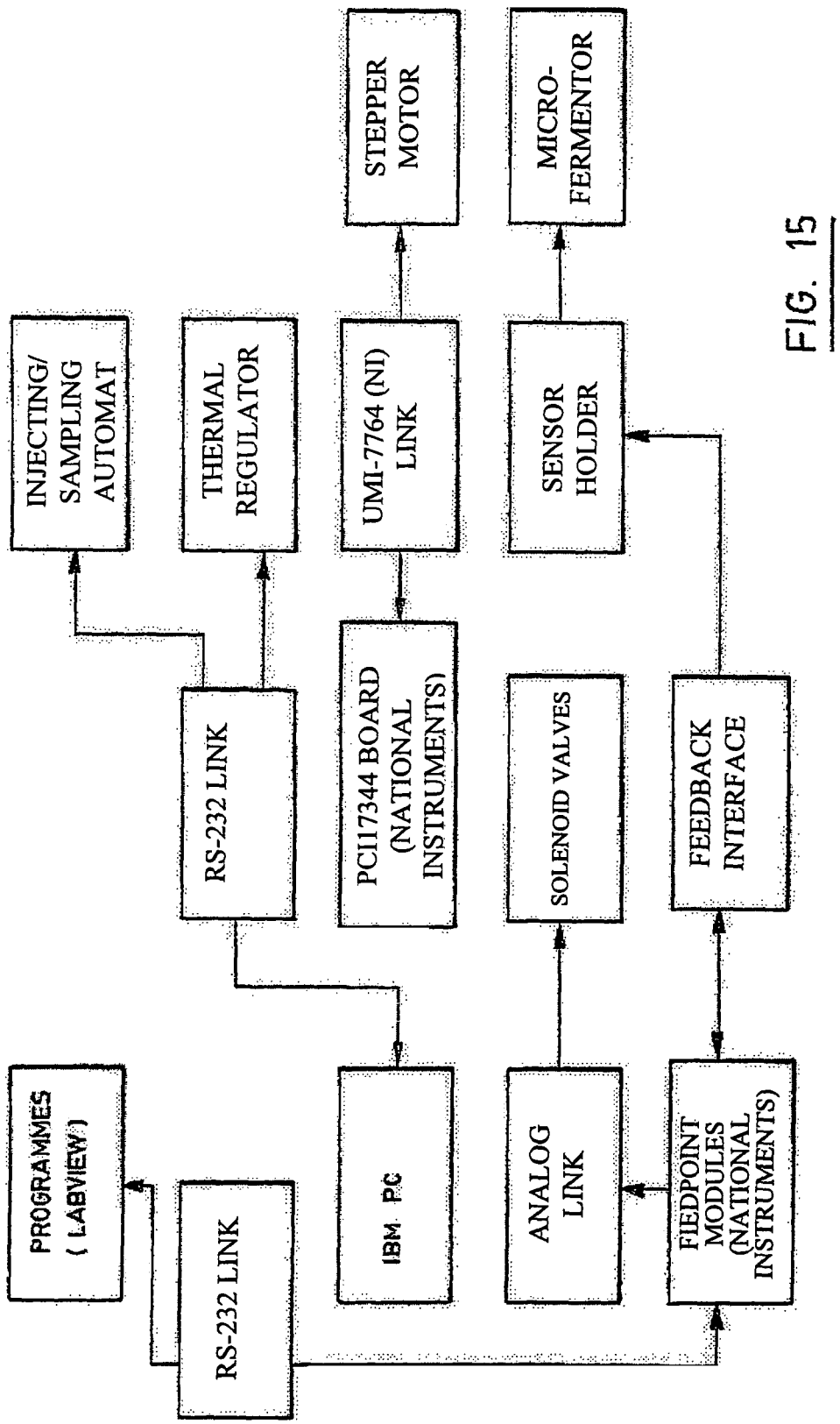
FIG. 15 shows an operating scheme of a micro-fermentor battery according to the present invention.

If the vial 33 is under depression:
the liquid is only drawn through the upper inlet (IN) towards the vial 33 as the two other paths are plugged (see FIG. 14F);

after some time has elapsed, the counter-pressure spring 43 equalizes the depression and the transfer is interrupted. But there is still inside the vial 33 a residual depression identical to the spring strength (see FIG. 14G);

the needle support 19 rises one step (or slowly) and releases the purging channel 37 (with the help of the return spring 31 of the piston 29 pushing the vial 33) without however fully releasing the needle 35. The air (this path should optionally comprise a sterilizing micro-filter) gets into the channel 37 and transfers the liquid which is still contained in the capillary tube in the purging device 39 and the vial 33;

the piston 29 pushes back at the end of the stroke the vial 33 and the pressing roller 23 comes back into position;

the up-down module brings back in high position the needle support 19 (see FIG. 14A); and the mobile guide positions again in its waiting area and the needles are sterilized by the heat from the mini-resistors.

The injecting/sampling automat 15 offers a new concept perfectly integrated into the micro-fermentor battery 3.

The automat 15 allows for actions to be slaves by means of injecting and sampling tubes being under pressure or depression. The volumes of the injected solutions and of the samples are predetermined. The device does not require any other external elements, such as solenoids, fermentor pressurizing, pumps, etc.

The automat 15 only needs one single line for injections and samplings; it offers the following advantages: compactness, minimum piping line (dead volume); high ergonomics; computing possibility to manage the location of each tube (traceability); no crossed contamination risk.

Using the one-way overpressure tubes and depression tubes simplifies the operations and makes them safer. At the laboratory level, pressurizing and underpressurizing can occur simply with the help of a sterile syringe under a laminar flux hood, preferably using double thickness corks. Other devices can be used.

Opening the pipes can occur at the level of the needle support 19 using a mechanical device, the cam (pressing roller 23), which is simple, robust and cheap, the movement of which being a function of the needle position 35 in the vial 33. The purging device 39 and the purging channel 37 allow to fully discharge without any additional control the pipes after the sampling operations.

Another alternative, simpler from the mechanical standpoint, but with a lower performance for the method, would be to use a needle support without a purging device and a purging channel. Such an alternative however needs, before each sampling operation, a purge which occurs through shifting the needle support towards a garbage tube or vial.

A third alternative for the needle support can be contemplated: this other device comprises a double or triple needle (one connected with the fermentor as before, one supplying the pressurized gas, one connected with the vacuum) for more complex operations (for example supplying or sampling high volumes).

The automat 15, integrated into the culture platform 1 in micro-reactor 3 batteries, offers a new concept for introducing solutions and samplings, bringing thus in parallel and in a fully automated way, cultures from the introduction of the pre-cultures up to the final storage operation.

Introducing liquids into the micro-fermentors can occur through different conventional means:

overpressure vials, containing any culture media or solutions, are connected to fermentors (these are practically at the atmospheric pressure, except if the effluent outlets are plugged) through pipes (in manifolds). Overlapped or proportional all or nothing (TOR) solenoid valves (able to be sterilized) are driven by the computer. Opening the latter allows the liquids to flow, upstream to downstream, by means of the pressure gradient. The flow rates are regulated by flow rate regulators or using capillary devices exerting variable loading losses (0.5 mm Teflon tube, for example). For a constant upstream pressure, the flow rates are significantly constant. These are a simple function of the capillary lengths; and syringes or a pump containing the solution to be introduced are connected to one or more fermentors by means of manifolds. The driven syringe pushing devices allow for a variable supply depending on the culture needs. The syringes have the advantage of having constant flow rates, whatever the viscosity of the media is.

Such devices can allow for the introduction of solutions, for example opening a solenoid or actuating the syringe pushing device, or sampling, for example blocking the outlet of gas effluents through closing one solenoid (hence, the fermentor being overpressurized) and allowing the sampling to pass through opening of another solenoid valve (a two-path nip solenoid valve can be therefore used, one normally closed at rest (purge), one normally opened (vent)).

However, such devices are adapted with more difficulty to the platform for several reasons:

bulkiness;

cost; and complex assembly.

The injecting/sampling automat 15 offers advantages both at the level of the performance of the device and in the automated implementation of the processes.

One of the advantages of the present invention lies at the level of the operation slaving by means of pressurized or underpressurized tubes. Thus, having available pressurized or underpressurized tubes with variable volumes considerably simplifies culture procedures, for example:

0.5 to 2 ml overpressure tubes, at 4° C., each contain the various pre-cultures at an exponential phase. At the time of the injection, the cultures (60 ml) are seeded at 1/20 (which is a conventional dilution);

2 ml tubes contain 0.5 to 2 ml or more of the inducer solution which are introduced at the appropriate DO; and 0.5 to 2 ml underpressure tubes will be used to receive samples taken. One ml is highly satisfactory to carry out the usual analyses.

Having one useful line at a time for injecting and sampling offers numerous advantages:

higher ergonomics to avoid multiple lines being often hard to identify, hence a higher operational ease and less contamination risk;

the volume of such a line is minimized in order to avoid dead volumes and culture losses, which is not the case when a pump is being used; and no crossed contamination by means of the principle of liquid circulation and needle sterilization.

The overpressurized tubes and the underpressurized tubes allow to develop one-way consumable products (glass or plastic tubes plugged by a septum, manifolds in supply lines with proven joints, etc.), specific for the present technology, able to contain ready-to-use solutions: inducers, antibiotics, particular media, etc., hence economical and practical advantages.

In addition, the pipe automatic sewage system further offers more simplicity in the operation.

The automatic achievement of a full and high quality culture involves:

exponential phase pre-cultures;
a follow-up of the culture measuring the evolution of the parameters, more particularly the cell concentration;
actions, such as the introduction of the inducer, at the selected time or at the selected DO;
sampling for evaluating the production with a view to monitoring it or optimizing it; and
storing cultures.

The injecting/sampling automat 15, integrated into the micro-fermentors 3, contributes to meeting these conditions, for example, in the case of recombinant cultures:
the pre-cultures obtained in the growth exponential phase are stored in such a condition on the automat racks at 4° C., thereby allowing to initiate the cultures in the reactors with reduced latency phases;
they are injected into the micro-fermentors according to the programme, for example, at a given time in the night, so as to have an exponential phase culture in the morning;
the cultures grow, often with different kinetics. When, for each culture, the inducing DO is obtained, the inducer is automatically introduced into the appropriate micro-fermentor;
samples are taken in order to calculate the protein production kinetics; and
at the end of the culture, after the set induction time, the cultures can be directly cooled down in the reactor or conveyed into storing vials.

The culture automation is a key factor for the standardization and optimization of culture procedures. It helps to a high score for good cultures, while facilitating, through an in line recording of the triggered operations and their influence on the cultures, construing the reasons for a lower or better production (involvement of the structure or the expression difficulty of the cloned genes: few codons, insoluble proteins under the form of inclusion bodies; effects of the components of the medium; of the temperature, etc.).

In the long run, the sampling tubes or the culture end tubes are stored on the automat racks which will be taken by a robot to be able to perform the subsequent steps of the culture processes: centrifugation, cell rupture or lysis, protein dosage, etc.

As far as traceability is concerned, tubes can be identified and thereby allow for the follow-up of the various operations.

The above described injecting/sampling automat integrated into the automated micro-fermentor platform makes it possible to have an efficient equipment in the field of micro-cultures being automated in parallel.

In addition to Genomics and Proteomics, numerous other applications are possible:
enrichment, selection, adaptation of micro-organisms to particular environments;
comparison of strains, microbial physiology;
development of culture media;
study of the simultaneous effects of the environmental multiparametric factors (predictive microbiology);
case of hard to cultivate strains (high latency and generation time);
optimization of the culture methods; scale-up;
study of biofilms;
depollution (decantation study; enrichment of strains, mixed cultures);
protein marking ($^{13}C$, $^{15}N$, selenomethionin, heavy water);
screening of strains;
screening of compounds of pharmaceutical interest;
Biotransformations; and
cell therapy; physiological condition.

The application areas cover numerous fields:
food processing industry;
pharmaceutical industry;
clinical microbiology;
environment (biofilms, polluting agents), depollution and treatments;
fermentation laboratories and industries; and
research.

The invention should be found a key tool in the field of chemistry and environment for reasons of cost reduction and injecting and sampling operations automated.

Some companies for 1 to 20 liter laboratory fermentors use the Labview® software for conducting the culture methods. Integrating such an automat in the Labview® environment according to the present invention could provide a significant advantage to this equipment.

Implantation of pH and $pO_2$ Micro-Electrodes for the Follow-Up and the Regulation of These Parameters The micro-fermentor platen 3 has been designed for receiving pH and $pO_2$ micro-electrodes, in a view to controlling the regulation of such parameters and ensuring optimum culture conditions. The various required gases flow by means of a 0.3 to 0.6 bar overpressure, from upstream to downstream. A programmable solenoid valve system allows to achieve optimum gaseous air/$O_2$ mixtures for obtaining very high cell concentrations (more than 100 DO for the *E. Coli* bacterium).

Maintaining the Culture System in Overpressure

In order to meet the sterility requirement in the bacterial cultures being processed, all the cultures are maintained in a light overpressure. For a higher safety, the liquid or gaseous effluents are channelled and processed chemically.

Bacteriological Culture Methods

The usage potentialities of the micro-fermentor culture automated platform have fully been demonstrated in the particular and very current field of the expression of heterologous recombinant proteins, in *E. coli* (*Mycobacterium* proteins—Genopole IP Project). Optimizing culture methods (developing specific culture media, optimizing oxygen transfers in reactors, determining the optimum conditions for the induction and the harvest) made it possible to reach very high expression levels in soluble proteins. Such results meet the objective of the present invention which comprises providing an automated production tool, combined with a know-how, for meeting the numerous international programmes of structural genomics.

Computerized Managing and Supervising of the Methods

The electronic and computerized environment being developed (National Instruments communication electronic interfaces and writing of programmes under the Labview® software) allows, for the eight cultures achieved in parallel, a graphical execution and a simplified follow-up of the processes in progress, at all their operating steps. Programming allows the independent automation of the eight (8) reactors to be managed, such as the phases of solute introduction, sampling, regulation of various parameters such as pH and $pO_2$, or cooling down at the culture end.

The platform as described herein corresponds to a new concept in the field of bacteriology, i.e. being able to conduct in parallel and in a fully automated way, miniature cultures in an integrated system under the form of reactor batteries.

Culture Reactors

The square section of the culture reactors allow to offer an optics adapted to the in line measurement of turbidity. The low 60 ml volume in the culture conditions which have been optimized is satisfactory for the production needs in biomass or in recombinant proteins with a view to a crystallographic or functional analysis of such proteins. Such a low volume allows for the reduction of the bulkiness of the batteries. Such a culture volume leads to a reduced use of sometimes expensive culture media. Using porous sintered materials for the dispersion of the aeration gases and using pure oxygen considerably increase the efficiency of the oxygen transfers, and advantageously replaces the mechanical or magnetic stirring operations. The architecture of such reactors allows for implanting on a platen pH and $pO_2$ micro-probes connected to electronic transmitters. Such sensors ensure a measurement of the evolution of those two parameters during the bacterial culture. A solenoid valve leads to a mixing of aeration gas (air and $O_2$) and is able to maintain a dissolved oxygen rate, as defined by the user. Regulating the pH is also contemplated through the addition of alkaline or acidic solutions. The computerized programme ensures the follow-up and the P.I.D. regulation of such parameters.

Process Management and Automation

It is meant under automation of miniature cultures, the possibility to trigger an event or a series of events in a programmed way and without any involvement from the user. The originality of the system according to the invention is that such an event triggering operation directly depends on a turbidity value as measured in line on the culture. Such a turbidity value is directly correlated to the cell density in the reactor and is a key parameter for all the cultures. The fact that such a turbidity measurement can be achieved nearly continuously, without any involvement from the operator and any disturbance of the cultures, allows for triggering, in parallel on all the cultures being processed, various functions nearly instantaneously, as soon as a particular turbidity set point has been reached. Such an automation is a guarantee of standardization and calibration of the conditions at which the cultures are achieved. Such criteria are particularly important in the studies of strain selection or method optimization.

Herein below are listed the specific advantages of an embodiment of the present invention on battery culture technologies marketed by DASGIP and INFORS companies and are to be noted the advantages that only the present invention can provide:

a miniaturization of culture cells: the developed reactors have a 60 ml volume and are similar to conventional fermentors because of the possibility to implant pH and $pO_2$ probes. The DASGIP and INFORS technologies suggest reactors with a minimum volume of 150 ml. Because of the reactor low volume, the batteries according to the invention have a reduced bulkiness adapted to the laboratory space constraints;

a guarantee of the culture standardization: the method is the only one on the market to provide a direct, sequential and in line measurement of the turbidity of all the cultures being processed by a single scrolling measurement cell. There are other systems based on indirect evaluations of the cell concentration through the measurement of various culture parameters (pH, oxygen consumption, redox potential, substrate concentrations, etc.). Such measurements require, for each culture, different sensors inserted into the reactor and subjected to drifts in the course of the operation. In the present case, the measuring system, being unique and located outside the reactor, provides a better stability guarantee at the response level. The present system allows to know and to compare in real time the growth phase of all the cultures achieved in parallel; and a process automation: generally speaking, the automation of a culture process has the objective of limiting at the most, even to fully remove, any involvement from the user on the process in progress. The advantages of such a robotized culture technology are numerous: standardization of tasks performed by the automat via very rapid, reliable and accurate mechanical operations; possibility to apply to the process a high flow rate production; possibility to achieve cultures even if the latter require time schedules incompatible with the user's presence; integration of the culture automated process into an automated processing line of the products of such a culture (centrifugation and processing of culture residues and supernatants, in line purification and analysis by other automats).

The culture automated platform technology according to the present invention is the only one to provide, with flexibility, all these advantages. The DASGIP and INFORS procedures actually correspond to a low volume (150 ml) reactor culture system in parallel, but are not fully adapted and designed for meeting the automation objectives.

On the more specific area of culture optimization, the automation allows to optimize the various steps of a culture method:

the inocula can be stopped in the growth exponential phase and stored in such a condition, allowing a culture start minimizing the latency phase;

during the cell growth, the automated control of the oxygen supplies as a function on the culture turbidity allows to work constantly at the most favourable $O_2$ concentration and to avoid, in case of a partial anaerobiosis, the production of acetate inhibiting the synthesis of recombinant proteins, or in the case of too a high $O_2$ concentration, the synthesis of stress proteins (including proteases able to hydrolyse the protein being produced);

the automated temperature changes, according to programmed sequences triggering depending on the in line measurement of the cell density or the value of other parameters, allow to adapt and to orient in the most narrow way the cell syntheses as desired by the user. It is thus possible to cultivate first cells at the temperature allowing for an optimum growth rate (30 or 37° C.) and to quickly obtain some biomass, and then, in order to favour the synthesis of soluble proteins, to trigger at a predefined cell density, an automated temperature decrease (at 15° C. or less if required) and an inducer introduction (IPTG for example) which is monitored. At the end of the induction phase, the temperature is automatically brought back to the selected temperature, for example 4° C., and thereby allows to maintain the culture in the optimum processing waiting conditions (case of night cultures); et sampling allowing to follow up the expression kinetics of a given protein is done automatically by the injecting/sampling automat.

The culture automation is a key factor for the standardization and optimization of culture procedures. It helps to obtain a high score for good cultures, while facilitating through an in line recording of the triggered operations and their influence on the cultures, construing the reasons for a lower or better production (involvement of the structure or of the expression difficulty of the cloned genes: few codons, insoluble proteins under the form of inclusion bodies; effects of the components of the medium; of the temperature, etc.).

The present invention provides for the implementation ease: the platform comprises a compact battery of eight (8) micro-reactors (that can be supplemented up to twelve (12) or more). The cheap easily maintained micro-fermentors are easy to insert into batteries and to connect reliably with the various gaseous and liquid flow pipes. The control graphic programmes are user-friendly via a visual presentation of the processes in progress on the control computer screen. The computerized interface has been developed for a quick management of the process by users. It allows for managing culture execution, accurate calibration of probes and scrolling turbidity sensor and allows, if required, to modify culture parameters as a function of the culture behaviour.

The various options or methods according to the present automated culture technology allow to open the way to numerous applications:

very low volume automated cultures for selecting new therapeutic usage molecules, oriented against bacterial strains maintained in an optimum growth or in conditions as predetermined by the research worker. Such cultures are achieved in aerated tubes (2 to 5 ml), supported on racks, with an in line measurement of the turbidity via the scrolling sensor and the programmed injection of any molecule being cultivated. Nowadays, the automated stirred micro-plate cultures, which are largely used in all the bio-medical projects, are the only one available for such a type of project. However, the growth of culture using such a technique is soon restricted by oxygen due to the passive transfer of gas towards the liquid phase. This technique is thus only compatible with the use of simple media and does not allow for inferring the behaviour of strains in complex media used in fermentation. Moreover, the expression levels of recombinant proteins in micro-plates remain very low;

the concept of the platform 1 can be adapted to batteries provided with very low volume or higher volume fermentors or reactors; and high volume automated cultures for the production of proteins intended for functional genomics studies. Such a technology will use culture reactors which are already designed and which are fully compatible with the turbidity in line measurement requirements and the various automated functions. Such reactors are cylindrical (from 125 to 500 ml) and have an adequate excrescence for the turbidity measurement. The turbidity in line measurement scrolling sensor passes successively in front of the battery reactor excrescences and positions at the level of the two parallel faces for a correct reading. In the approach of systematic studies of the proteins coded by genes of sequenced genomes, numerous proteins only express very weakly. Such proteins are toxic for the bacterial strains hosting the corresponding genes, or have biochemical and functional characteristics (membrane proteins) little favourable to the expression under a soluble form. Increasing the culture volumes, coupled with the advantages from the automation, should allow to compensate for such low expression levels and to thereby meet the expectations from the functionality studies of such proteins.

Such a technology could also be applied to the optimization of methods that are to be transferred to high production scales:

miniature reactor cultures for the molecular marking of proteins, with a view to NMR and crystallography studies. The use of decreased volumes reduces the cost of very expensive marked media;

cultures for example in batch, fed batch, turbidostate, cyclic cultures, continuous cultures in chemostat, for strain evolution or selection studies and physiological studies. With the low volume of cultures (60 ml), it is possible to achieve long duration cultures without having to frequently change les service tanks, which is a tedious change, likely to cause contaminations;

implantation of the present technology of PSM (Microbiological Safety Station) culture automated platform or in confined premises of the P2 or P3 type, with remote culture follow-up and monitoring (Internet, warning e-mail, etc.); and development of one-way consumable products, specific for the present technology: plastic culture reactors, ready-to-use culture media, etc.

The above described equipment is an original and evolutional concept in the field of automated micro-cultures.

In addition to Genomics and Proteomics, numerous other applications are possible, including some minor adaptations (mainly at the level of monitoring programmes), for example:

enrichment, selection, adaptation of micro-organisms to particular environments;

comparison of strains, microbial physiology;

development of culture media;

study of the simultaneous effects of the environmental multiparametric factors (predictive microbiology);

case of hard to cultivate strains (high latency and generation time);

optimization of the culture methods; scale-up;

study of biofilms;

screening of strains;

screening of compounds of pharmaceutical interest;

biotransformations; and protein marking ($^{13}C$, $^{15}N$, selenomethionin, heavy water); and cell therapy.

The application areas cover numerous fields:

food processing industry;

pharmaceutical industry;

clinical microbiology;

environment (biofilms, polluting agents), depollution and treatments;

fermentation laboratories and industries; and research.

The table herein below gives system validation results according to a preferred embodiment of the present invention. There is shown the expression level of a number of proteins using the conventional methods for producing proteins or using the system according to the present invention.

COMPARISON OF AMOUNTS OF SOLUBLE RECOMBINANT PROTEINS, OBTAINED IN 1 LITER STIRRED FERBACH AND IN 60 ML MULTI-MICRO FERMENTORS ACCORDING TO THE PRESENT INVENTION

| | | Yield (mg/affinity/purified soluble protein) | |
| --- | --- | --- | --- |
| Produced proteins | Molecular weight Kda | Ferbach of 1 liter LB media | Bioreactor of 60 ml HD media according to the present invention |
| 1 | 19.8 | 15 | 100 |
| 2 | 23.5 | 60 | 60 |
| 3 | 28.7 | 20 | 20 |
| 4 | 25.3 | 20 | 22 |
| 5 | 55 | 47 | 40 |
| 6 | 21.56 | 68 | 67 |
| 7 | 27.17 | 29 | 31 |
| 8 | 17.6 | 29 | 35 |
| 9 | 21 | 4.6 | 8.4 |
| 10 | 24.2 | 40 | 50 |
| 11 | 24.2 | 78 | 94 |
| 12 | 26.4 | 37 | 52 |
| 13 | 27.7 | 38 | 66 |
| 14 | 25.19 | 40 | 66 |
| 15 | 24.31 | 42 | 56 |
| 16 | 20.9 | 150 | 150 |

Although the present invention has been explained hereinabove with preferred embodiment, it should be understood that the invention is not limited to this particular embodiment and that various changes and modifications can be brought to it without departing from the scope or the spirit of the invention.

What is claimed is:

1. An automated and robotized platform including a battery of micro-fermentors having a useful culture volume ranging from 2 mL to 500 mL, each configured to contain a cell culture, the robotized platform comprising:
   a fork shaped mobile sensor holder configured to receive at least two external sensors, the mobile sensor holder including a sensor moving element configured to move the external sensors from one of the micro-fermentors to another of the micro-fermentors and to allow the real time measurement of a turbidity property of each cell culture contained in each micro-fermentor;
   a monitoring and processing element configured to receive, in real time measurements, the optical property from the external sensor and to monitor, in real time, a movement of the mobile sensor holder, and
   a system configured to regulate a temperature of each micro-fermentor including a Peltier effect autonomous regulating system, the regulation of the temperature by Peltier effect being independent and programmable for each micro-fermentor, at a temperature range of $-5°$ C. to $80°$ C., wherein
   each of the at least two external sensors includes a turbidity-measuring sensor including an emitting diode and a receiving diode and is situated at a different height on the mobile sensor holder.

2. The robotized platform according to claim 1, wherein the external sensor is configured as an absorbency, fluorescence, luminescence, phosphorescence, or colorimetry sensor, or as other sensor measuring an electromagnetic radiation.

3. The robotized platform according to claim 1 or 2, wherein the sensor moving element includes either
   at least one mobile carriage arranged on at least one linear rail, a stepper motor, a driving system connecting the motor with the carriage, and a monitoring element connected with the stepper motor and being configured to ensure linear movement of the mobile carriage; or
   an arm or another system configured to allow a circular movement and a monitoring element connected to the arm or the another system configured to ensure circular movement of the arm or the another system.

4. The robotized platform according to claim 1, further comprising a sampling and injecting system arranged on a mobile support and connected with a moving system, either independent from or integral with the mobile sensor holder.

5. The robotized platform according to claim 1, wherein the battery of micro-fermentors is configured to produce cell cultures.

6. The robotized platform according to claim 1, wherein the battery of micro-fermentors is configured to optimize cell culture methods.

7. The robotized platform according to claim 5, wherein the battery of micro-fermentors is configured to allow analysis of gene expression mechanisms.

8. The robotized platform according to claim 7, wherein the battery of micro-fermentors is configured to allow analysis of genes involved in cell adherence mechanisms.

9. The robotized platform according to claim 1, wherein the battery of micro-fermentors is configured to allow study of physical and physicochemical mechanisms.

10. The robotized platform according to claim 4, wherein the sampling and injecting system is configured to increase $O_2$ concentration or to inject solutions configured to regulate pH in response to a measurement of the optical property.

11. The robotized platform according to claim 1, wherein the turbidity-measuring sensor is configured to make optical density measurements in a range of 0.05 OD to 300 OD.

12. An automated and robototized platform including a battery of micro-fermentors having a useful culture volume ranging from 2 mL to 500 mL, each configured to contain a cell culture, the robotized platform comprising:
   a fork shaped mobile sensor holder configured to receive at least two external sensors, the mobile sensor holder including a sensor moving element configured to move the external sensors from one of the micro-fermentors to another of the micro-fermentors and to allow the real time measurement of a turbidity property of each cell culture contained in each micro-fermentor;
   each of said at least two external sensors including a turbidity-measuring sensor including an emitting diode and a receiving diode and being situated at different heights on the mobile sensor holder;
   a monitoring and processing element configured to receive, in real time measurements, the turbidity measurements from the external sensors and to monitor in real time, a movement of the mobile sensor holder;
   a sampling and injecting system arranged above the micro-fermentors on a mobile support and connecting with a moving system, either independent from or integral with the mobile sensor holder; and
   a system configured to regulate a temperature of each micro-fermentor or including a Peltier effect autonomous regulating system, the regulation of the temperature by Peltier effect being independent and programmable for each micro-fermentor, at a temperature range of $-5°$ C. to $80°$ C.

13. An automated and robototized platform including a battery of micro-fermentors having a useful culture volume ranging from 2 mL to 500 mL, each configured to contain a cell culture, the robotized platform comprising:
   a fork shaped mobile sensor holder configured to receive at least two external sensors, the mobile sensor holder including a sensor moving element configured to move the external sensors from one of the micro-fermentors to another of the micro-fermentors and to allow the real time measurement of a turbidity property of each cell culture contained in each micro-fermentor;
   each of said at least two external sensors including a turbidity-measuring sensor including an emitting diode and a receiving diode and being situated at different heights on the mobile sensor holder;
   a monitoring and processing element configured to receive, in real time measurements, the turbidity measurements from the external sensors and to monitor in real time, a movement of the mobile sensor holder;
   a sampling and injecting system arranged above the micro-fermentors on a mobile support and connecting with a moving system, either independent from or integral with the mobile sensor holder;
   said sampling and injecting system comprising a needle support which comprises a pressing roller for crushing a flexible pipe, a spring return mobile piston having a head for centering and maintaining a vial neck during operation and a notch to lift the pressing roller for allowing fluid circulation, a needle connected with the flexible pipe and a purging channel parallel to the needle; and a system configured to regulate a temperature of each micro-fermentor including a Peltier effect autonomous regulating system, the regulation of the temperature by Peltier effect being independent and programmable for each micro-fermentor, at a temperature range of −5° C. to 80° C.

14. The robotized platform according to claim 1, wherein the fork shaped mobile sensor holder has at least one side that is open.

15. The robotized platform according to claim 1, wherein the fork shaped mobile sensor holder has at least two arms, each arm including at least one of the at least two external sensors.

* * * * *